(12) United States Patent
Eldred et al.

(10) Patent No.: US 8,093,281 B2
(45) Date of Patent: Jan. 10, 2012

(54) INDAZOLES AS GLUCOCORTICOID RECEPTOR LIGANDS

(75) Inventors: Colin David Eldred, Stevenage (GB); David House, Stevenage (GB); Graham George Adam Inglis, Stevenage (GB); Simon John Fawcett MacDonald, Stevenage (GB); Philip Alan Skone, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 748 days.

(21) Appl. No.: 11/910,935

(22) PCT Filed: Apr. 12, 2006

(86) PCT No.: PCT/EP2006/003551
§ 371 (c)(1),
(2), (4) Date: Oct. 23, 2008

(87) PCT Pub. No.: WO2006/108699
PCT Pub. Date: Oct. 19, 2006

(65) Prior Publication Data
US 2009/0074675 A1  Mar. 19, 2009

(30) Foreign Application Priority Data

Apr. 14, 2005 (GB) .................................. 0507597.3
Aug. 9, 2005 (GB) .................................. 0516375.3
Nov. 9, 2005 (GB) .................................. 0522882.0

(51) Int. Cl.
*A61K 31/416* (2006.01)
*C07D 231/56* (2006.01)
(52) U.S. Cl. .................................. 514/403; 548/362.5
(58) Field of Classification Search ............... 548/362.5; 514/403
See application file for complete search history.

(56) References Cited

FOREIGN PATENT DOCUMENTS

| WO | 03/082280 A | 10/2003 |
|---|---|---|
| WO | 2004/063163 A | 7/2004 |
| WO | 2005/003098 A | 1/2005 |
| WO | 2005/030213 A | 4/2005 |

OTHER PUBLICATIONS

Balant et al., "Metabolic Considerations, etc.," in Manfred ed, Burger's Medicinal Chemistry and Drug Discovery, 5th ed. vol. 1: Principles and Practice, John Wiley & Sons, Inc., 1995.*
Vippagunta et al., "Crystalline Solids", Advanced Drug Delivery Reviews 48 (2001) 3-26.*
Guillory (in Brittain ed.), "Polymorphism, etc.," NY: Marcel Dekker, Inc., 1999, 1-2, 183-226.*
Reich, et al., Ring formation with the elimination of a nitro group II; Bull. Soc. Chim. Fr.: 1917; 21; 111; Beilstein Institut.

* cited by examiner

*Primary Examiner* — Patricia Morris
(74) *Attorney, Agent, or Firm* — Robert J. Smith

(57) ABSTRACT

A compound of formula (I):

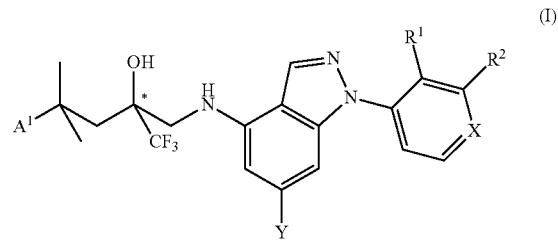

* = chiral centre wherein
$A^1$ represents 2,3-dihydro-1-benzofuran-7-yl, 5-fluoro-2-methoxy-phenyl or 5-fluoro-2-hydroxy-phenyl;
X represents —$C(R^3)$— or nitrogen;
when X represents —$C(R^3)$—, $R^2$ represents hydrogen and $R^1$ represents fluorine, $R^3$ represents hydrogen or fluorine,
when X represents —$C(R^3)$— and $R^2$ and $R^1$ each represent hydrogen, $R^3$ represents hydrogen, hydroxy, methoxy or fluorine,
when X represents —$C(R^3)$— and $R^2$ represents hydroxy, methoxy, —$CO_2CH_3$ or —$CO_2CH_2CH_3$, $R^1$ and $R^3$ each represent hydrogen,
when X represents nitrogen, $R^1$ and $R^2$ each represent hydrogen; and
Y represents H or methyl;
or a physiologically functional derivative thereof.

12 Claims, No Drawings

INDAZOLES AS GLUCOCORTICOID RECEPTOR LIGANDS

This application is filed pursuant to 35 U.S.C. §371 as a United States National Phase Application of International Patent Application Serial No. PCT/EP2006/003551 filed Apr. 12, 2006, which claims priority from Great Britain Application Nos. 0507597.3, 0516375.3, and 0522882.0 filed in the United Kingdom on Apr. 14, 2005, Aug. 9, 2005, and Nov. 9, 2005 respectively.

The present invention relates to non-steroidal compounds, pharmaceutical compositions comprising the compounds and the use of the compounds for the manufacture of a medicament, particularly for the treatment of inflammation.

Nuclear receptors are a class of structurally related proteins involved in the regulation of gene expression. The steroid hormone receptors are a subset of this family whose natural ligands typically comprise endogenous steroids such as estradiol (estrogen receptor), progesterone (progesterone receptor) and cortisol (glucocorticoid receptor). Man-made ligands to these receptors play an important role in human health, in particular the use of glucocorticoid agonists to treat a wide range of inflammatory conditions.

Glucocorticoids exert their actions at the glucocorticoid receptor (GR) through at least two intracellular mechanisms, transactivation and transrepression (see: Schacke, H., Docke, W-D. & Asadullah, K. (2002) *Pharmacol and Therapeutics* 96:23-43; Ray, A., Siegel, M. D., Prefontaine, K. E. & Ray, P. (1995) *Chest* 107:139 S; and Konig, H., Ponta, H., Rahmsdorf, H. J. & Herrlich, P. (1992) *EMBO J.* 11:2241-2246). Transactivation involves direct binding of the glucocorticoid receptor to distinct deoxyribonucleic acid (DNA) glucocorticoid response elements (GREs) within gene promoters, usually but not always increasing the transcription of the downstream gene product. Recently, it has been shown that the GR can also regulate gene expression through an additional pathway (transrepression) in which the GR does not bind directly to DNA. This mechanism involves interaction of the GR with other transcription factors, in particular NFkB and AP1, leading to inhibition of their pro-transcriptional activity (Schacke, H., Docke, W-D. & Asadullah, K. (2002) *Pharmacol and Therapeutics* 96:23-43; and Ray, A., Siegel, M. D., Prefontaine, K. E. & Ray, P. (1995) *Chest* 107:139 S). Many of the genes involved in the inflammatory response are transcriptionally activated through the NFkB and AP1 pathways and therefore inhibition of this pathway by glucocorticoids may explain their anti-inflammatory effect (see: Barnes, P. J. & Adcock, I. (1993) *Trend Pharmacol Sci* 14:436-441; and Cato, A. C. & Wade, E. (1996) *Bioessays* 18: 371-378).

Despite the effectiveness of glucocorticoids in treating a wide range of conditions, a number of side-effects are associated with pathological increases in endogenous cortisol or the use of exogenous, and particularly systemically administered, glucocorticoids. These include reduction in bone mineral density (Wong, C. A., Walsh, L. J., Smith, C. J. et al. (2000) *Lancet* 355:1399-1403), slowing of growth (Allen, D. B. (2000) *Allergy* 55: suppl 62, 15-18), skin bruising (Pauwels, R. A., Lofdahl, C. G., Latinen, L. A. et al. (1999) *N Engl J Med* 340:1948-1953), development of cataracts (Cumming, R. G., Mitchell, P. & Leeder, S. R. (1997) *N Engl J Med* 337:8-14) and dysregulation of lipid and glucose metabolism (Faul, J. L., Tormey, W., Tormey, V. & Burke, C. (1998) *BMJ* 317:1491; and Andrews, R. C. & Walker, B. R. (1999) *Clin Sci* 96:513-523). The side-effects are serious enough often to limit the dose of glucocorticoid that can be used to treat the underlying pathology leading to reduced efficacy of treatment.

It has been suggested that excessive activation of the transactivation-GRE pathway may mediate some of these side-effects (see Schacke, H., Docke, W-D. & Asadullah, K. (2002) *Pharmacol and Therapeutics* 96:23-43). Development of glucocorticoids that selectively modulate the transrepression pathway compared with the transactivation pathway may therefore have a superior anti-inflammatory to side-effect therapeutic index, allowing more effective and safer treatment of the patient. Such glucocorticoids could be used to treat more effectively and more safely the whole spectrum of disease currently treated by current glucocorticoids.

Current known glucocorticoids have proved useful in the treatment of inflammation, tissue rejection, auto-immunity, various malignancies, such as leukemias and lymphomas, Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia and Little's syndrome.

Glucocorticoids are especially useful in disease states involving systemic inflammation such as inflammatory bowel disease, systemic lupus erythematosus, polyarteritis nodosa, Wegener's granulomatosis, giant cell arteritis, rheumatoid arthritis, osteoarthritis, seasonal rhinitis, allergic rhinitis, vasomotor rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoids have also been used as immunostimulants and repressors and as wound healing and tissue repair agents.

Glucocorticoids have also found use in the treatment of diseases such as inflammatory scalp alopecia, panniculitis, psoriasis, discoid lupus erythemnatosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform and cutaneous T-cell lymphoma.

WO00/32584, WO02/10143, WO03/082827, WO03/082280, DE10261874, WO05/003098 and WO05/030213 disclose certain non-steroidal anti-inflammatory agents.

In one embodiment, the present invention provides compounds of formula (I):

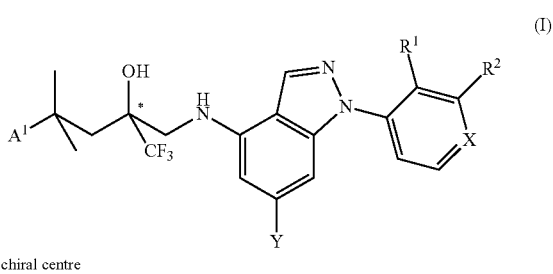

* = chiral centre wherein
A¹ represents 2,3-dihydro-1-benzofuran-7-yl, 5-fluoro-2-methoxy-phenyl or 5-fluoro-2-hydroxy-phenyl;
X represents —C(R³)— or nitrogen;
when X represents —C(R³)—, R² represents hydrogen and R¹ represents fluorine, R³ represents hydrogen or fluorine,
when X represents —C(R³)— and R² and R¹ each represent hydrogen, R³ represents hydrogen, hydroxy, methoxy or fluorine,
when X represents —C(R³)— and R² represents hydroxy, methoxy, —CO$_2$CH$_3$ or —CO$_2$CH$_2$CH$_3$, R¹ and R³ each represent hydrogen,
when X represents nitrogen, R¹ and R² each represent hydrogen; and
Y represents H or methyl;
and physiologically functional derivatives thereof (hereinafter "compounds of the invention").

In another embodiment, the present invention provides compounds of formula (IA):

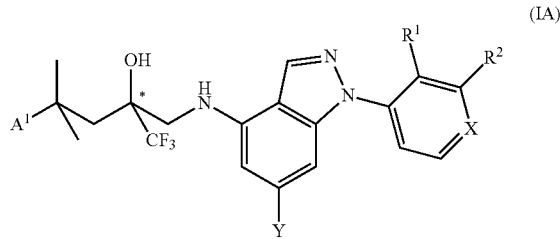

(IA)

* = chiral centre wherein
A¹ represents 2,3-dihydro-1-benzofuran-7-yl, 5-fluoro-2-methoxy-phenyl or 5-fluoro-2-hydroxy-phenyl;
X represents —C(R³)— or nitrogen;
when X represents —C(R³)—, R² represents hydrogen and R¹ represents fluorine, R³ represents hydrogen or fluorine,
when X represents —C(R³)— and R² and R¹ each represent hydrogen, R³ represents hydrogen, methoxy or fluorine,
when X represents —C(R³)— and R² represents —CO$_2$CH$_3$ or —CO$_2$CH$_2$CH$_3$, R¹ and R³ each represent hydrogen,
when X represents nitrogen, R¹ and R² each represent hydrogen; and
Y represents H or methyl;
and physiologically functional derivatives thereof.

In another embodiment, the present invention provides compounds of formula (IB):

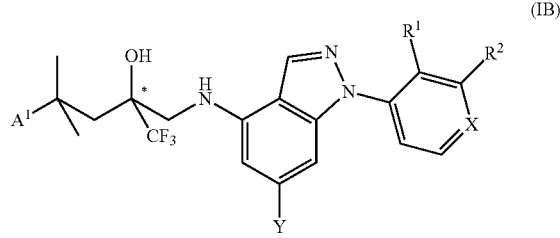

(IB)

* = chiral centre wherein
A¹ represents 2,3-dihydro-1-benzofuran-7-yl or 5-fluoro-2-(methoxy)-phenyl;
X represents —C(R³)— or nitrogen;
when X represents —C(R³)—, R² represents hydrogen and R¹ represents fluorine, R³ represents hydrogen or fluorine,
when X represents —C(R³)— and R² and R¹ each represent hydrogen, R³ represents hydrogen, methoxy or fluorine,
when X represents —C(R³)— and R² represents —CO$_2$CH$_3$ or —CO$_2$CH$_2$CH$_3$, R¹ and R³ each represent hydrogen,
when X represents nitrogen, R¹ and R² each represent hydrogen; and
Y represents H or methyl;
and physiologically functional derivatives thereof.

In a further embodiment, the present invention provides compounds of formula (IC):

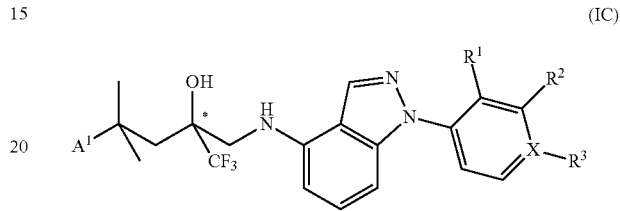

(IC)

* = chiral centre wherein
A¹ represents 2,3-dihydro-1-benzofuran-7-yl or 5-fluoro-2-(methoxy)-phenyl;
X represents carbon or nitrogen;
when X represents carbon and R² represents hydrogen and R¹ represents fluorine, R³ represents hydrogen or fluorine;
when X represents carbon and R² and R¹ represent hydrogen, R³ represents hydrogen, methoxy or fluorine;
when X represents carbon and R² represents —CO$_2$Et, R¹ and R³ each represent hydrogen;
when X represents nitrogen, R¹ and R² represent hydrogen.

When X represents nitrogen in a compound of formula (IC), it will be understood that the group R³ will be absent.

Compounds of formula (I) contain one chiral centre. A single enantiomer or mixture of enantiomers (eg. racemic mixture) may be preferred. In one embodiment, the invention provides compounds of formula (I) of the 2R configuration.

In one embodiment, the invention provides compounds of formula (I) wherein A¹ represents 2,3-dihydro-1-benzofuran-7-yl or 5-fluoro-2-(methoxy)-phenyl. In another embodiment, the invention provides compounds of formula (I) wherein A¹ represents 5-fluoro-2-(methoxy)-phenyl. In a further embodiment, the invention provides compounds of formula (I) wherein A¹ represents 5-fluoro-2-hydroxy-phenyl.

In one embodiment, the invention provides compounds of formula (I) wherein X represents —C(R³)—. In a further embodiment, the invention provides compounds of formula (I) wherein X represents nitrogen.

In one embodiment, the invention provides compounds of formula (I) wherein X represents —C(R³)—, R² represents hydrogen, R¹ represents fluorine and R³ represents hydrogen or fluorine. In another embodiment, the invention provides compounds of formula (I) wherein X represents —C(R³)—, R² represents hydrogen, R¹ represents fluorine and R³ represents fluorine. In another embodiment, the invention provides compounds of formula (I) wherein X represents —C(R³)—, R² and R¹ each represent hydrogen and R³ represents hydrogen, hydroxy, methoxy or fluorine. In another embodiment, the invention provides compounds of formula (I) wherein X represents —C(R³)—, R² and R¹ each represent hydrogen and R³ represents hydrogen, methoxy or fluorine. In another embodiment, the invention provides compounds of formula (I) wherein X represents —C($R^3$)—, $R^2$ represents hydroxy, methoxy, —$CO_2CH_3$ or —$CO_2CH_2CH_3$, and $R^1$ and $R^3$ each represent hydrogen. In another embodiment, the invention provides compounds of formula (I) wherein X represents —C($R^3$)—, $R^2$ represents —$CO_2CH_3$ or —$CO_2CH_2CH_3$, and $R^1$ and $R^3$ each represent hydrogen. In another embodiment, the invention provides compounds of formula (I) wherein X represents —C($R^3$)—, $R^2$ represents —$CO_2CH_2CH_3$, and $R^1$ and $R^3$ each represent hydrogen. In a further embodiment, the invention provides compounds of formula (I) wherein X represents nitrogen, and $R^2$ and $R^1$ each represent hydrogen.

In one embodiment, the invention provides compounds of formula (I) wherein Y represents hydrogen. In a further embodiment, the invention provides compounds of formula (I) wherein Y represents methyl.

In one embodiment, the compound of formula (I) is:

1,1,1-trifluoro-4-[5-fluoro-2-(methyloxy)phenyl]-2-({[1-(2-fluorophenyl)-1H-indazol-4-yl]amino}methyl)-4-methyl-2-pentanol;

1,1,1-trifluoro-4-[5-fluoro-2-(methyloxy)phenyl]-2-({[1-(4-fluorophenyl)-1H-indazol-4-yl]amino}methyl)-4-methyl-2-pentanol;

1,1,1-trifluoro-4-[5-fluoro-2-(methyloxy)phenyl]-4-methyl-2-[({1-[4-(methyloxy)phenyl]-1H-indazol-4-yl}amino)methyl]-2-pentanol;

2-({[1-(2,4-difluorophenyl)-1H-indazol-4-yl]amino}methyl)-1,1,1-trifluoro-4-[5-fluoro-2-(methyloxy)phenyl]-4-methyl-2-pentanol;

1,1,1-trifluoro-4-[5-fluoro-2-(methyloxy)phenyl]-4-methyl-2-({[1-(4-pyridinyl)-1H-indazol-4-yl]amino}methyl)-2-pentanol;

ethyl 3-(4-{[4-[5-fluoro-2-(methyloxy)phenyl]-2-hydroxy-4-methyl-2-(trifluoro methyl) pentyl]amino}-1H-indazol-1-yl)benzoate;

1,1,1-trifluoro-4-[5-fluoro-2-(methyloxy)phenyl]-4-methyl-2-{[(1-phenyl-1H-indazol-4-yl)amino]methyl}-2-pentanol;

4-(2,3-dihydro-1-benzofuran-7-yl)-1,1,1-trifluoro-4-methyl-2-{[(1-phenyl-1H-indazol-4-yl)amino]methyl}-2-pentanol;

ethyl 3-(4-{[4-(2,3-dihydro-1-benzofuran-7-yl)-2-hydroxy-4-methyl-2-(trifluoromethyl)pentyl]amino}-1H-indazol-1-yl)benzoate;

4-(2,3-dihydro-1-benzofuran-7-yl)-1,1,1-trifluoro-2-({[1-(2-fluorophenyl)-1H-indazol-4-yl]amino}methyl)-4-methyl-2-pentanol;

4-(2,3-dihydro-1-benzofuran-7-yl)-1,1,1-trifluoro-2-({[1-(4-fluorophenyl)-1H-indazol-4-yl]amino}methyl)-4-methyl-2-pentanol;

2-({[1-(2,4-difluorophenyl)-1H-indazol-4-yl]amino}methyl)-4-(2,3-dihydro-1-benzofuran-7-yl)-1,1,1-trifluoro-4-methyl-2-pentanol;

4-(2,3-dihydro-1-benzofuran-7-yl)-1,1,1-trifluoro-4-methyl-2-({[1-(4-pyridinyl)-1H-indazol-4-yl]amino}methyl)-2-pentanol;

methyl 3-(4-{[4-[5-fluoro-2-(methyloxy)phenyl]-2-hydroxy-4-methyl-2-(trifluoro methyl) pentyl]amino}-1H-indazol-1-yl)benzoate;

1,1,1-trifluoro-4-[5-fluoro-2-(methyloxy)phenyl]-4-methyl-2-{[(6-methyl-1-phenyl-1H-indazol-4-yl)amino]methyl}-2-pentanol;

2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol;

4-(2,3-dihydro-1-benzofuran-7-yl)-1,1,1-trifluoro-4-methyl-2-{[(6-methyl-1-phenyl-1H-indazol-4-yl)amino]methyl}-2-pentanol;

2-[3-({[1-(2,4-difluorophenyl)-6-methyl-1H-indazol-4-yl]amino}methyl)-4,4,4-trifluoro-3-hydroxy-1,1-dimethylbutyl]-4-fluorophenol;

1,1,1-trifluoro-4-[5-fluoro-2-(methyloxy)phenyl]-4-methyl-2-[({6-methyl-1-[4-(methyloxy)phenyl]-1H-indazol-4-yl}amino)methyl]-2-pentanol;

4-(4-{[4-[5-fluoro-2-(methyloxy)phenyl]-2-hydroxy-4-methyl-2-(trifluoromethyl)pentyl]amino}-6-methyl-1H-indazol-1-yl)phenol;

4-fluoro-2-[4,4,4-trifluoro-3-hydroxy-3-({[1-(4-hydroxyphenyl)-6-methyl-1H-indazol-4-yl]amino}methyl)-1,1-dimethylbutyl]phenol;

1,1,1-trifluoro-4-[5-fluoro-2-(methyloxy)phenyl]-4-methyl-2-[({6-methyl-1-[3-(methyloxy)phenyl]-1H-indazol-4-yl}amino)methyl]-2-pentanol;

3-(4-{[4-[5-fluoro-2-(methyloxy)phenyl]-2-hydroxy-4-methyl-2-(trifluoromethyl)pentyl]amino}-6-methyl-1H-indazol-1-yl)phenol;

4-fluoro-2-[4,4,4-trifluoro-3-hydroxy-3-({[1-(3-hydroxyphenyl)-6-methyl-1H-indazol-4-yl]amino}methyl)-1,1-dimethylbutyl]phenol;

1,1,1-trifluoro-4-[5-fluoro-2-(methyloxy)phenyl]-2-({[1-(2-fluorophenyl)-6-methyl-1H-indazol-4-yl]amino}methyl)-4-methyl-2-pentanol;

1,1,1-trifluoro-4-[5-fluoro-2-(methyloxy)phenyl]-2-({[1-(4-fluorophenyl)-6-methyl-1H-indazol-4-yl]amino}methyl)-4-methyl-2-pentanol;

ethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate;

4-(2,3-dihydro-1-benzofuran-7-yl)-1,1,1-trifluoro-4-methyl-2-[({1-[4-(methyloxy)phenyl]-1H-indazol-4-yl}amino)methyl]-2-pentanol; or a physiologically functional derivative thereof.

In another embodiment, the compound of formula (I) is:

1,1,1-trifluoro-4-[5-fluoro-2-(methyloxy)phenyl]-2-({[1-(2-fluorophenyl)-1H-indazol-4-yl]amino}methyl)-4-methyl-2-pentanol;

1,1,1-trifluoro-4-[5-fluoro-2-(methyloxy)phenyl]-2-({[1-(4-fluorophenyl)-1H-indazol-4-yl]amino}methyl)-4-methyl-2-pentanol;

1,1,1-trifluoro-4-[5-fluoro-2-(methyloxy)phenyl]-4-methyl-2-[({1-[4-(methyloxy)phenyl]-1H-indazol-4-yl}amino)methyl]-2-pentanol;

2-({[1-(2,4-difluorophenyl)-1H-indazol-4-yl]amino}methyl)-1,1,1-trifluoro-4-[5-fluoro-2-(methyloxy)phenyl]-4-methyl-2-pentanol;

1,1,1-trifluoro-4-[5-fluoro-2-(methyloxy)phenyl]-4-methyl-2-({[1-(4-pyridinyl)-1H-indazol-4-yl]amino}methyl)-2-pentanol;

ethyl 3-(4-{[4-[5-fluoro-2-(methyloxy)phenyl]-2-hydroxy-4-methyl-2-(trifluoro methyl) pentyl]amino}-1H-indazol-1-yl)benzoate;

1,1,1-trifluoro-4-[5-fluoro-2-(methyloxy)phenyl]-4-methyl-2-{[(1-phenyl-1H-indazol-4-yl)amino]methyl}-2-pentanol;

4-(2,3-dihydro-1-benzofuran-7-yl)-1,1,1-trifluoro-4-methyl-2-{[(1-phenyl-1H-indazol-4-yl)amino]methyl}-2-pentanol; or a physiologically functional derivative thereof.

In another embodiment, the compound of formula (I) is:

2-({[1-(2,4-difluorophenyl)-1H-indazol-4-yl]amino}methyl)-1,1,1-trifluoro-4-[5-fluoro-2-(methyloxy)phenyl]-4-methyl-2-pentanol (enantiomer B);

ethyl 3-(4-{[4-[5-fluoro-2-(methyloxy)phenyl]-2-hydroxy-4-methyl-2-(trifluoro methyl) pentyl]amino}-1H-indazol-1-yl)benzoate (enantiomer B);

1,1,1-trifluoro-4-[5-fluoro-2-(methyloxy)phenyl]-4-methyl-2-{[(6-methyl-1-phenyl-1H-indazol-4-yl)amino]methyl}-2-pentanol (enantiomer B);
2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol (enantiomer A); or
a physiologically functional derivative thereof.

In another embodiment, the compound of formula (I) is:
2-({[1-(2,4-difluorophenyl)-1H-indazol-4-yl]amino}methyl)-1,1,1-trifluoro-4-[5-fluoro-2-(methyloxy)phenyl]-4-methyl-2-pentanol (enantiomer B);
ethyl 3-(4-{[4-[5-fluoro-2-(methyloxy)phenyl]-2-hydroxy-4-methyl-2-(trifluoro methyl) pentyl]amino}-1H-indazol-1-yl)benzoate (enantiomer B);
1,1,1-trifluoro-4-[5-fluoro-2-(methyloxy)phenyl]-4-methyl-2-{[(6-methyl-1-phenyl-1H-indazol-4-yl)amino]methyl}-2-pentanol (enantiomer B);
2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol (enantiomer A);
2-[3-({[1-(2,4-difluorophenyl)-6-methyl-1H-indazol-4-yl]amino}methyl)-4,4,4-trifluoro-3-hydroxy-1,1-dimethylbutyl]-4-fluorophenol; or
a physiologically functional derivative thereof.

In a further embodiment, the compound of formula (I) is:
2-({[1-(2,4-difluorophenyl)-1H-indazol-4-yl]amino}methyl)-1,1,1-trifluoro-4-[5-fluoro-2-(methyloxy)phenyl]-4-methyl-2-pentanol (enantiomer B);
1,1,1-trifluoro-4-[5-fluoro-2-(methyloxy)phenyl]-4-methyl-2-{[(6-methyl-1-phenyl-1H-indazol-4-yl)amino]methyl}-2-pentanol (enantiomer B);
2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol (enantiomer A);
4-(2,3-dihydro-1-benzofuran-7-yl)-1,1,1-trifluoro-4-methyl-2-{[(6-methyl-1-phenyl-1H-indazol-4-yl)amino]methyl}-2-pentanol;
4-(2,3-dihydro-1-benzofuran-7-yl)-1,1,1-trifluoro-4-methyl-2-{[(6-methyl-1-phenyl-1H-indazol-4-yl)amino]methyl}-2-pentanol (enantiomer B);
4-(4-{[4-[5-fluoro-2-(methyloxy)phenyl]-2-hydroxy-4-methyl-2-(trifluoromethyl)pentyl]amino}-6-methyl-1H-indazol-1-yl)phenol;
4-fluoro-2-[4,4,4-trifluoro-3-hydroxy-3-({[1-(4-hydroxyphenyl)-6-methyl-1H-indazol-4-yl]amino}methyl)-1,1-dimethylbutyl]phenol;
4-fluoro-2-[4,4,4-trifluoro-3-hydroxy-3-({[1-(3-hydroxyphenyl)-6-methyl-1H-indazol-4-yl]amino}methyl)-1,1-dimethylbutyl]phenol;
4-fluoro-2-[4,4,4-trifluoro-3-hydroxy-3-({[1-(3-hydroxyphenyl)-6-methyl-1H-indazol-4-yl]amino}methyl)-1,1,1-dimethylbutyl]phenol (enantiomer B);
1,1,1-trifluoro-4-[5-fluoro-2-(methyloxy)phenyl]-2-({[1-(2-fluorophenyl)-6-methyl-1H-indazol-4-yl]amino}methyl)-4-methyl-2-pentanol (enantiomer A);
1,1,1-trifluoro-4-[5-fluoro-2-(methyloxy)phenyl]-2-({[1-(4-fluorophenyl)-6-methyl-1H-indazol-4-yl]amino}methyl)-4-methyl-2-pentanol (enantiomer B); or
a physiologically functional derivative thereof.

The invention includes physiologically functional derivatives of the compound of formula (I). By the term "physiologically functional derivative" is meant a chemical derivative of a compound of formula (I) having the same physiological function as a free compound of formula (I), for example, by being convertible in the body thereto and includes any pharmaceutically acceptable esters, carbonates, carbamates, salts and solvates of compounds of formula (I), and solvates of any pharmaceutically acceptable esters, carbonates, carbamates or salts of compounds of formula (I), which, upon administration to the recipient, are capable of providing (directly or indirectly) compounds of formula (I) or active metabolite or residue thereof. Thus one embodiment of the invention embraces compounds of formula (I) and salts and solvates thereof. Another embodiment of the invention embraces compounds of formula (I) and salts thereof. A further embodiment of the invention embraces compounds of formula (I).

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds of formula (I) and their pharmaceutically acceptable salts, solvates, and physiologically functional derivatives.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

Examples of solvates include hydrates.

The compounds of the invention are expected to have potentially beneficial anti-inflammatory or anti-allergic effects, particularly upon topical administration, demonstrated by, for example, their ability to bind to the glucocorticoid receptor and to illicit a response via that receptor. Hence, the compounds of the invention may be of use in the treatment of inflammatory and/or allergic disorders.

Examples of disease states in which the compounds of the invention are expected to have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease (COPD), interstitial lung disease, and fibrosis; inflammatory bowel conditions such as ulcerative colitis and Crohn's disease; and auto-immune diseases such as rheumatoid arthritis.

It will be appreciated by those skilled in the art that reference herein to treatment extends to prophylaxis as well as the treatment of established conditions.

As mentioned above, compounds of the invention are expected to be of use in human or veterinary medicine, in particular as anti-inflammatory and/or anti-allergic agents.

There is thus provided as a further aspect of the invention a compound of the invention for use in human or veterinary medicine, particularly in the treatment of patients with inflammatory and/or allergic conditions, such as rheumatoid arthritis, asthma, COPD, allergy and/or rhinitis.

Further provided is a compound of the invention for use in the treatment of patients with skin disease such as eczema, psoriasis, allergic dermatitis, neurodermatitis, pruritis and/or hypersensitivity reactions.

According to another aspect of the invention, there is provided the use of a compound of the invention for the manufacture of a medicament for the treatment of patients with inflammatory and/or allergic conditions, such as rheumatoid arthritis, asthma, COPD, allergy and/or rhinitis.

According to yet to another aspect of the invention, there is provided the use of a compound of the invention for the manufacture of a medicament for the treatment of patients with skin disease such as eczema, psoriasis, allergic dermatitis, neurodermatitis, pruritis and/or hypersensitivity reactions.

In a further or alternative aspect, there is provided a method for the treatment of a human or animal subject with an inflammatory and/or allergic condition such as rheumatoid arthritis, asthma, COPD, allergy and/or rhinitis, which method comprises administering to said human or animal subject an effective amount of a compound of the invention.

In yet a further or alternative aspect, there is provided a method for the treatment of a human or animal subject with skin disease such as eczema, psoriasis, allergic dermatitis, neurodermatitis, pruritis and/or hypersensitivity reactions, which method comprises administering to said human or animal subject an effective amount of a compound of the invention.

The compounds of the invention may be formulated for administration in any convenient way, and the invention therefore also includes within its scope pharmaceutical compositions comprising a compound of the invention together, if desirable, in admixture with one or more physiologically acceptable diluents or carriers.

Further, there is provided a process for the preparation of such pharmaceutical compositions which comprises mixing the ingredients.

The compounds of the invention may, for example, be formulated for oral, buccal, sublingual, parenteral, local rectal administration or other local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (eg. eye or nose drops), solutions/suspensions for nebulisation, suppositories, pessaries, retention enemas and chewable or suckable tablets or pellets (eg. for the treatment of aphthous ulcers) or liposome or microencapsulation preparations.

Formulations for administration topically to the nose for example, for the treatment of rhinitis, include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of the invention may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg. oleic acid, lecithin or an oligolactic acid or derivative eg. as described in WO94/21229 and WO98/34596 and cosolvents eg. ethanol.

There is thus provided as a further aspect of the invention a pharmaceutical aerosol formulation comprising a compound of the invention and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain from 20 μg to 10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (eg., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of the invention in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (eg., see Byron, above and WO96/32099). Preferably the canister is fitted with a cap assembly, wherein a drug-metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (eg. DF10, DF30, DF60), Bespak plc, UK (eg. BK300, BK357) and 3M-Neotechnic Ltd, UK (eg. Spraymiser™).

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms may be preferred as described below.

The compounds of the invention may in general be given by internal administration in cases wherein systemic glucocorticoid receptor agonist therapy is indicated.

Slow release or enteric coated formulations may be advantageous, particularly for the treatment of inflammatory bowel disorders.

In some embodiments, the compounds of formula (I) will be formulated for oral administration. In other embodiments, the compounds of formula (I) will be formulated for inhaled administration.

The compounds and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment of the invention encompasses combinations comprising a compound of the invention together with a $\beta_2$-adrenoreceptor agonist, and/or an anticholinergic, and/or a PDE-4 inhibitor.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising of a compound of the invention together with a $\beta_2$-adrenoreceptor agonist.

Examples of $\beta_2$-adrenoreceptor agonists include salmeterol (which may be a racemate or a single enantiomer, such as the R-enantiomer), salbutamol (e.g. as racemate or a single enantiomer such as the R-enantiomer, formoterol (e.g. as racemate or a single diastereomer such as the R,R-diastereomer), salmefamol, fenoterol, carmoterol, etanterol, naminterol, clenbuterol, pirbuterol, flerobuterol, reproterol, bambuterol, indacaterol or terbutaline and salts thereof, for example the xinafoate (1-hydroxy-2-naphthalenecarboxylate) salt of salmeterol, the sulphate salt or free base of salbutamol or the fumarate salt of formoterol. In one embodiment, the $\beta_2$-adrenoreceptor agonists are long-acting $\beta_2$-adrenoreceptor agonists, for example those having a therapeutic effect over a 24 hour period.

Examples of $\beta_2$-adrenoreceptor agonists may include those described in WO02/66422A, WO02/270490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]foramide,
N-2{2-[4-(3-phenyl-4-methoxyphenyl)aminophenyl]ethyl}-2-hydroxy-2-(8-hydroxy-2(1H)-quinolinon-5-yl)ethylamine, and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, and salts thereof.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

In one embodiment, the invention provides the use of the compounds the invention in combination with a phosphodiesterase 4 (PDE4) inhibitor, for example in the case of a formulation adapted for inhalation. The PDE4-specific inhibitor may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3- cyclopropylmethoxy-4-difluoromethoxyphenyl)cyclohexan-1-ol]. Another compound is cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), PCT/EP2003/014867 (Glaxo Group Ltd) and PCT/EP2004/005494 (Glaxo Group Ltd).

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Other anticholinergic agents include compounds of formula (XXI), which are disclosed in U.S. patent application No. 60/487,981:

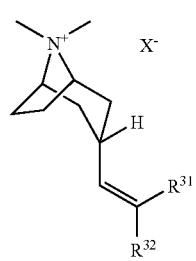

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^−$ represents an anion associated with the positive charge of the N atom. $X^−$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application No. 60/511,009:

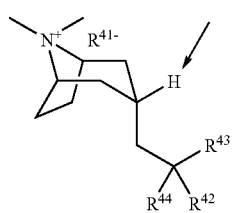

(XXII)

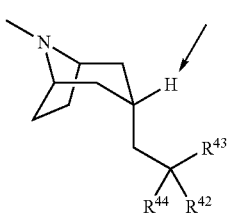

(XXIII)

wherein:
the H atom indicated is in the exo position;
$R^{41−}$ represents an anion associated with the positive charge of the N atom; $R^{41−}$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having from 6 to 10 carbon atoms), heterocycloalkyl (having from 5 to 6 carbon atoms) and N or O as the heteroatom, heterocycloalkyl-alkyl (having from 6 to 10 carbon atoms) and N or O as the heteroatom, aryl, optionally substituted aryl, heteroaryl, and optionally substituted heteroaryl;

$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl $(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —$CN$, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, —$CH_2N(R^{48})CONH(R^{47})$;

$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl $(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

Further compounds include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Examples of antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine and cetirizine.

Examples of anti-histamines include loratidine, desloratidine, fexofenadine and cetirizine.

The invention thus provides, in a further aspect, a combination comprising a compound of formula (I) and/or a pharmaceutically acceptable salt, solvate or physiologically functional derivative thereof together with a PDE4 inhibitor.

The invention thus provides, in a further aspect, a combination comprising a compound of formula (I) and/or a pharmaceutically acceptable salt, solvate or physiologically functional derivative thereof together with a $\beta_2$-adrenoreceptor agonist.

The invention thus provides, in a further aspect, a combination comprising a compound of formula (I) and/or a pharmaceutically acceptable salt, solvate or physiologically functional derivative thereof together with an anticholinergic.

The invention thus provides, in a further aspect, a combination comprising a compound of formula (I) and/or a pharmaceutically acceptable salt, solvate or physiologically functional derivative thereof together with an antihistamine.

The invention thus provides, in a further aspect, a combination comprising a compound of formula (I) and/or a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of formula (I) and/or a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation.

Appropriate doses of known therapeutic agents will readily be appreciated by those skilled in the art.

The invention thus provides, in a further aspect, a pharmaceutical composition comprising a combination of a compound of the invention together with another therapeutically active agent.

The invention thus provides, in a further aspect, a pharmaceutical composition comprising a combination of a compound of the invention together with a PDE4 inhibitor.

The invention thus provides, in a further aspect, a pharmaceutical composition comprising a combination of a compound of the invention together with a 2-adrenoreceptor agonist.

A process according to the invention for the preparation of compounds of formula (I) comprises reaction of an epoxide of formula (II):

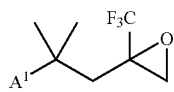
(II)

wherein $A^1$ is as defined above for compounds of formula (I), with a 4-amino-1-arylindazole of formula (III):

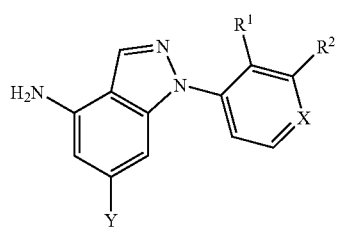
(III)

wherein $R^1$, $R^2$, X and Y are as defined above for compounds of formula (I).

The epoxide opening reaction may be performed in a dipolar aprotic solvent such as N,N-dimethylformamide at a non-extreme temperature in the range 0-100° C., most commonly 20° C. (or room temperature) in the presence of a strong base such as potassium tert-butoxide. Alternatively, these epoxide opening reactions may be performed in a microwave reactor in the absence of solvent or with a small amount of a high boiling point non-nucleophilic solvent such as N-methylpyrrolidinone at a high temperature in the range 100-200° C., most commonly 150° C. Alternatively the epoxide opening reactions may be catalysed by the inclusion of ytterbium(III) triflate as described in *Synthetic Communications* 2003, 33, 2989-2994 and *Bioorg. Med. Chem. Letters.* 2001, 11, 1625-1628.

Compounds of formula (II) wherein $A^1$ represent 5-fluoro-2-methoxy-phenyl or 2,3-dihydro-1-benzofuran-7-yl are described in racemic form in WO 04/063163. The compound of formula (II) in which $A^1$ represents 5-fluoro-2-methoxy-phenyl has also been described as separate enantiomers in WO 05/234250, WO05/040145 and in *Bioorg. Med. Chem. Letters.* 2006, 16, 654-657.

Compounds of formula (III) are novel and form another aspect of the invention and may be prepared by reaction of a 1H-indazol-4-amine (IV):

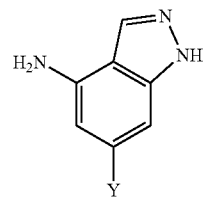
(IV)

wherein Y is as defined above for compounds of formula (I), with aryl iodides of formula (V)

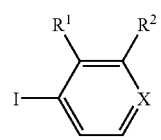
(V)

wherein $R^1$, $R^2$ and X are as defined above for compounds of formula (I).

The reaction of (IV) with (V) may be performed in the presence of a copper(I) catalyst, such as copper(I) iodide and a weak base such as potassium carbonate or potassium phosphate and an amine ligand such as L-proline, cyclohexanediamine, N,N'-dimethylcyclohexanediamine or N,N'-dimethylethylenediamine in a variety of solvents including toluene, dioxane, N,N-dimethylformamide, N,N-dimethylacetamide and dimethylsulfoxide at a temperature in the range 60-160° C., most typically 110° C. Representative procedures are reported in the literature: *Synthesis* 2005, 3, 496-499, *J. Org. Chem.*, 2004, 69, 5578-5587 and *J. Am. Chem. Soc.*, 2001, 123, 7727-7729.

Alternatively compounds of formula (III) may be prepared by similar reaction of a 4-nitro-1H-indazole (VI)

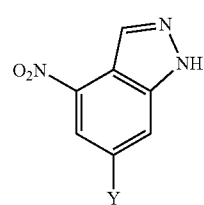
(VI)

wherein Y is as defined above for compounds of formula (I), with the aryl iodides (V) followed by reduction of the nitro group by, for example, hydrogenation over palladium on carbon.

An alternative process for the preparation of compounds of formula (I) comprises reaction of an amine of formula (VII):

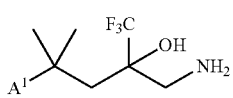
(VII)

wherein A¹ is as defined above for compounds of formula (I) with a 4-bromo-1-arylindazole of formula (VIII):

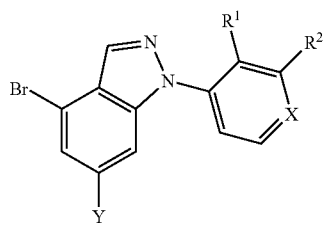

(VIII)

wherein R¹, R², X and Y are as defined above for compounds of formula (I).

This coupling reaction may be conveniently carried out using palladium catalysis of the type described by Buchwald in *Topics in Current Chemistry*, 2002, 219, 131-209. For example, the coupling reaction may be conducted using tris (dibenzylideneacetone)dipalladium(0), racemic-BINAP (2,2'-bis(diphenylphosphino)-1,1'-binaphthyl) and sodium tert-butoxide in toluene at reflux temperature or using microwave heating.

The compound of formula (VII) wherein A¹ represents 5-fluoro-2-methoxy-phenyl is known in racemic form (WO 05/003098, WO 03/082827). Compounds of formula (VII) may also be prepared by opening epoxides of formula (II) with benzylamine followed by removal of the benzyl group by hydrogenolysis using, for example, palladium on carbon as catalyst.

Individual enantiomers of compounds of formula (VII) may be obtained, for example, by separation by HPLC on a chiral column of the racemic material (VII) or a protected version (IX) thereof;

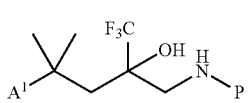

(IX)

wherein the group A¹ is as defined above for compounds of formula (I), and P represents a protecting group which is removed following enantiomer separation.

In one embodiment, P represents a benzyloxycarbonyl (CBZ), or benzyl protecting group. However, those skilled in the art could envisage the use of other protecting groups as alternatives. The CBZ or benzyl protecting groups may be removed by, for example, hydrogenolysis over a suitable catalyst such as palladium on carbon.

Where this protecting group P in compound (IX) contains an additional chiral centre of defined stereochemistry, for example, in the (R)-1-phenylethylamine derivative (X)

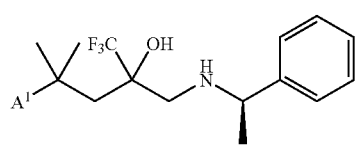

(X)

wherein the group A¹ are as defined above for compounds of formula (I), the resulting diastereoisomers may be separated by chromatography on a non-chiral or chiral support. As before, deprotection by hydrogenolysis following isomer separation provides the single enantiomers of compound (VII).

Compounds of formula (IX) may be prepared directly by protection of the racemic amine (VII). Alternatively intermediates of formula (IX) and (X) may be prepared by the reaction of the epoxide (II) with an amine P—NH₂.

The epoxide opening reaction may be performed in a dipolar aprotic solvent such as N,N-dimethylformamide at a non-extreme temperature in the range 0-100° C., most commonly 20° C. (or room temperature) in the presence of a strong base such as potassium tert-butoxide. Alternatively, these epoxide opening reactions may be performed in a microwave reactor in the absence of solvent or with a small amount of a high boiling point non-nucleophilic solvent such as N-methylpyrrolidinone at a high temperature in the range 100-200° C., most commonly 150° C. For reactions with (R)-(+)-1-phenylethylamine the epoxide opening to give (X) may be conveniently performed in ethanol solution at 50° C.

Compounds of formula (VIII) are novel and form another aspect of the invention and may be prepared by cyclisation of a hydrazone of formula (XI)

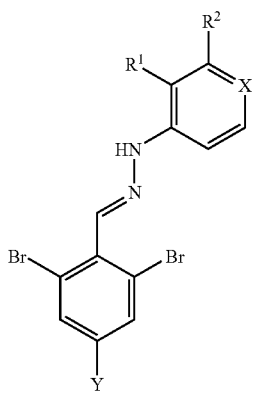

(XI)

wherein R¹, R², X and Y are as defined above for compounds of formula (I).

This intramolecular N-arylation may be conducted using palladium catalysis of the type described by Buchwald in *Topics in Current Chemistry*, 2002, 219, 131-209. For example, the cyclisation may be effected using tris(dibenzylideneacetone)dipalladium(0), racemic-BINAP (2,2'-bis (diphenylphosphino)-1,1'-binaphthyl) and tripotassium phosphate in toluene or 1,4-dioxane at reflux temperature.

Hydrazones of formula (XI) may be prepared by reaction of an aldehyde of formula (XII)

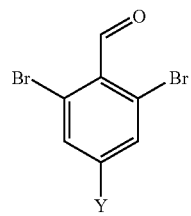

(XII)

wherein Y is as defined above for compounds of formula (I), with an aryl hydrazine of formula (XIII)

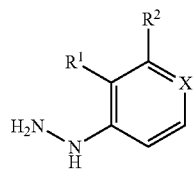

(XIII)

wherein $R^1$, $R^2$ and X are as defined above for compounds of formula (I).

Aldehydes of formula (XII) are known and may be prepared as described by Lulinski and Serwatowski in *J. Org. Chem.*, 2003, 68, 5384-5387

Aryl hydrazines (XIII) are either commercially available or may be prepared from the corresponding aniline by treatment with nitrous acid generated in situ from sodium nitrite followed by subsequent reduction of the resulting aryldiazonium ions with tin(II) chloride according to standard literature procedures (see, for example, *J Med Chem* 1991, 34, 2895; *J Med Chem* 2000 43: 4707, *J Med Chem* 2003 46: 2012).

Compounds of formula (I) in which $A^1$ represents 5-fluoro-2-hydroxy-phenyl may be prepared by reaction of the compounds of formula (I) in which $A^1$ represents 5-fluoro-2-methoxy-phenyl with, for example, boron tribromide in dichloromethane solution or by treatment with lithium iodide in N-methylpyrrolidinone using microwave heating at 220° C.

Compounds of formula (I) may be prepared in the form of mixtures of enantiomers when mixtures of isomers are used as intermediates in the synthesis. For example, the use of a compound of formula (II) or (VII) as a racemic mixture of enantiomers will lead to a mixture of enantiomers in the final product. These isomers may, if desired, be separated by conventional methods (e.g. HPLC on a chiral column).

Alternatively, separation of isomers may be performed earlier in the synthesis, for example individual isomers of compounds of formula (II) or (VII) may be employed which may obviate the need to perform a separation of isomers as a final stage in the synthesis. The later process is, in theory, more efficient and is therefore preferred.

Compositions comprising a compound of the invention also constitute an aspect of the invention.

In addition, processes for preparing formulations including one or more compounds of formula (I) form an aspect of this invention.

Solvates of compounds of formula (I), physiologically functional derivatives thereof or salts thereof, which are not physiologically acceptable may be useful as intermediates in the preparation of other compounds of formula (I), physiologically functional derivatives thereof or salts thereof.

Compounds of the invention may be expected to demonstrate good anti-inflammatory properties, with predictable pharmacokinetic and pharmacodynamic behaviour. They also may be expected to have an attractive side-effect profile, demonstrated, for example, by increased selectivity for the glucocorticoid receptor over the progesterone receptor and are expected to be compatible with a convenient regime of treatment in human patients.

The invention will now be illustrated by way of the following non-limiting examples.

EXAMPLES

Synthetic Experimental

Abbreviations

| | |
|---|---|
| $CDCl_3$ | Deuterochloroform |
| DMSO | Dimethylsulphoxide |
| EtOH | Ethanol |
| DCM | Dichloromethane |
| DMF | Dimethylformamide |
| Me | Methyl |
| MeOH | Methanol |
| $NH_3$ | Ammonia |
| HCl | Hydrochloric acid |
| Et | Ethyl |
| EtOAc | Ethyl acetate |
| NMR | Nuclear magnetic resonance |
| LCMS | Liquid chromatography/mass spectrometry |
| AcOH | Acetic acid |
| KOH | Potassium hydroxide |
| NMP | N-methylpyrrolidinone |
| MeCN | Acetonitrile |
| BINAP | (2,2'-bis(diphenylphosphino)-1,1'-binaphthyl) |
| SPE | Solid phase extraction |

Chromatographic Purification

Chromatographic purification was performed using pre-packed silica gel cartridges, in many cases using a Flashmaster II system. The Flashmaster II is an automated multi-user flash chromatography system, available from Argonaut Technologies Ltd, which utilises disposable, normal phase, SPE cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

NMR $^1$H NMR spectra were recorded in either $CDCl_3$ or DMSO-$d_6$ on either a Bruker DPX 400 or Bruker Avance DRX or Varian Unity 400 spectrometer all working at 400 MHz. The internal standard used was either tetramethylsilane or the residual protonated solvent at 7.25 ppm for $CDCl_3$ or 2.50 ppm for DMSO-$d_6$.

Microwave Heating

Heating by microwave was carried out in an Explorer System Discover oven supplied by CEM.

Mass Directed Autopreparative HPLC

Purifications were carried out using a Micromass ZQ platform. The column was a 100 mm×20 mm Supelco LCABZ++ with stationary phase particle size of 5 μm.

Solvents:
  A: water+0.1% formic acid
  B: MeCN:water 95:5+0.05% formic acid
Gradient 50-90% B over 10 minutes
Flow rate 20 mL/min
LCMS System
  The LCMS system used was as follows:
  Column: 3.3 cm×4.6 mm ID, 3 μm ABZ+PLUS from Supelco
  Flow Rate: 3 ml/min
  Injection Volume: 5 μl
  Temp: RT
  UV Detection Range: 215 to 330 nm Solvents:
A: 0.1% Formic Acid+10 mMolar Ammonium Acetate.
B: 95% Acetonitrile+0.05% Formic Acid

|  | Time | A % | B % |
|---|---|---|---|
| Gradient: | 0.00 | 100 | 0 |
|  | 0.70 | 100 | 0 |
|  | 4.20 | 0 | 100 |
|  | 5.30 | 0 | 100 |
|  | 5.50 | 100 | 0 |

Intermediate 1:
1-(2-Fluorophenyl)-1H-indazol-4-amine

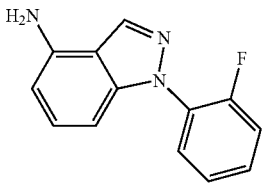

1H-Indazol-4-amine (1.83 g, 10 mmol), copper (I) iodide (95 mg. 0.5 mmol) and potassium phosphate (4.46 g, 21 mmol) were stirred together. The flask was evacuated and refilled with argon twice. To the flask was then added trans-N,N'-dimethyl-1,2-cyclohexanediamine (320 μL, 2 mmol), 2-fluoro-1-iodobenzene (2.66 g, 12 mmol) and toluene (30 mL) and the mixture was heated at 110° C. overnight. The reaction mixture was diluted with EtOAc, filtered through Celite to remove inorganics and the Celite pad was washed successively with EtOAc until the solvent ran clear. The reaction mixture was evaporated and the residue was purified by column chromatography eluting with dichloromethane then with dichloromethane:EtOAc 9:1 to give the title compound as a yellow oil (1.19 g) which solidified on standing.

$^1$H-NMR: (DMSO-$d_6$, 400 MHz) δ 8.41 (s, 1H), 7.60 (t, 1H), 7.58-7.47 (m, 2H), 7.40 (m, 1H), 7.10 (t, 1H), 6.44 (m, 1H), 6.30 (d, 1H), 5.98 (s, 2H)

Intermediate 2:
1-(4-Fluorophenyl)-1H-indazol-4-amine

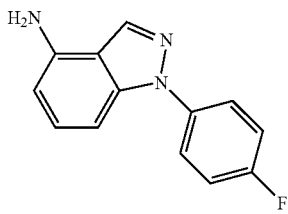

Similarly prepared to Intermediate 1 from 1H-indazol-4-amine and 4-fluoro-1-iodobenzene.

$^1$H-NMR: (DMSO-$d_6$, 400 MHz) δ 8.40 (s, 1H), 7.75 (m, 2H), 7.40 (m, 2H), 7.15 (t, 1H), 6.87 (d, 1H), 6.32 (d, 1H), 6.0 (s, 2H)

Intermediate 3:
1-[4-(Methyloxy)phenyl]-1H-indazol-4-amine

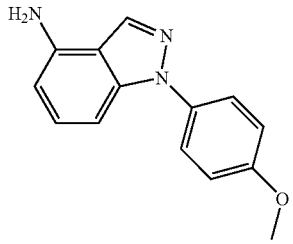

Similarly prepared to Intermediate 1 from 1H-indazol-4-amine and 1-iodo-4-(methyloxy)benzene.

$^1$H-NMR: (DMSO-$d_6$, 400 MHz) δ 8.35 (s, 1H), 7.60 (m, 2H), 7.12 (m, 3H), 6.8 (d, 1H), 6.25 (d, 1H), 5.95 (s, 2H), 3.81 (s, 3H)

Intermediate 4:
1-(2,4-Difluorophenyl)-1H-indazol-4-amine

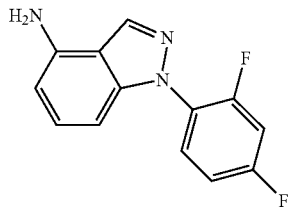

Similarly prepared to Intermediate 1 from 1H-indazol-4-amine and 2,4-difluoro-1-iodobenzene.

$^1$H-NMR: (DMSO-$d_6$, 400 MHz) δ 8.40 (s, 1H), 7.68 (m, 1H), 7.60 (m, 1H), 7.30 (m, 1H), 7.08 (t, 1H), 6.42 (m, 1H), 6.3 (d, 1H), 6.0 (s, 2H)

Intermediate 5: 1-(4-Pyridinyl)-1H-indazol-4-amine

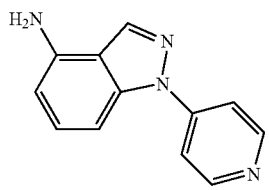

Similarly prepared to intermediate 1 from 1H-indazol-4-amine and 4-iodopyridine.

$^1$H-NMR: (DMSO-$d_6$, 400 MHz) δ 8.68 (d, 2H), 8.54 (s, 1H), 7.85 (d, 2H), 7.22 (t, 1H), 7.15 (d, 1H), 6.38 (d, 1H), 6.11 (s, 2H)

Intermediate 6: Ethyl 3-(4-amino-1H-indazol-1-yl)benzoate

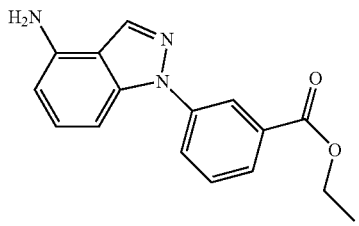

Similarly prepared to Intermediate 1 from 1H-indazol-4-amine and ethyl 3-iodobenzoate.
¹H-NMR: (DMSO-d₆, 400 MHz) δ 8.45 (s, 1H), 8.28 (s, 1H), 8.05 (m, 1H), 7.93 (m, 1H), 7.72 (t, 1H), 7.2 (t, 1H), 6.95 (d, 1H), 6.36 (d, 1H), 6.05 (s, 2H), 4.38 (q, 2H), 1.35 (t, 3H)

Intermediate 7: 4-Nitro-1-phenyl-1H-indazole

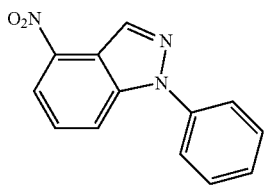

2,6-Dinitrobenzaldehyde (2.8 g, 14 mmol) (which may be prepared according to Reich, Gaigailian, *Chem. Ber.*, 46, (1913), 2382) and phenylhydrazine (1.7 g, 17 mmol) were dissolved in a mixture of EtOH (20 mL) and AcOH (2 mL) resulting in a red solution. After stirring for 2 hours the solution was concentrated to a red solid which was dissolved in EtOH (250 mL) and a solution of KOH (2 g) in water (30 mL) was added. After stirring for 2 hours the solution was concentrated to a black solid which was dissolved in EtOAc (1 L), washed with 1N HCl (3×500 mL), saturated sodium bicarbonate and brine (250 mL). The organic solution was dried and concentrated to a brown solid which was applied to a silica column. Elution with a 10%-50% gradient of EtOAc in hexane isolated the title compound as a yellow solid.
¹H-NMR: (CDCl₃, 400 MHz) δ 8.85 (s, 1H), 8.22 (d, 1H), 8.06 (d, 1H), 7.70 (m, 2H), 7.6 (m, 3H), 7.46 (m, 1H)

Intermediate 8: 1-Phenyl-1H-indazol-4-amine hydrochloride

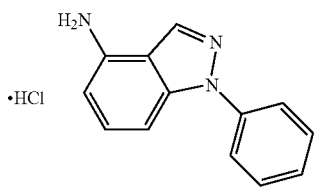

4-Nitro-1-phenyl-1H-indazole (Intermediate 7) was dissolved in EtOAc (200 mL) then 10% Pd/C (500 mg) was added and the mixture was stirred under a hydrogen atmosphere for 2 hours. Filtration through Celite and concentration of the filtrate gave a yellow oil which was dissolved in ether (100 mL). A solution of 4N HCl in dioxan (10 mL) was added slowly resulting in a yellow precipitate which was filtered off to give the title compound as a yellow solid (2.5 g).
¹H-NMR: (DMSO-d₆, 400 MHz) δ 8.4 (s, 1H), 7.71 (m, 2H), 7.55 (t, 2H), 7.35 (t, 1H), 7.22 (t, 1H), 7.14 (m, 1H), 6.53 (d, 1H), 5.40 (broad s)

Intermediate 9: Methyl 3-(4-amino-1H-indazol-1-yl)benzoate

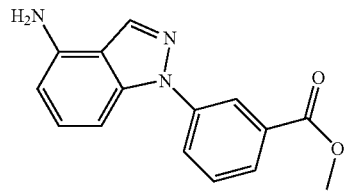

1H-Indazol-4-amine (81 mg, 0.61 mmol) and methyl 3-iodobenzoate (160 mg, 0.61 mmol) were dissolved in DMF (1 mL) in a microwave tube. Copper (I) iodide (23 mg, 0.12 mmol), trans-N,N'-dimethyl-1,2-cyclohexanediamine (34 mg, 0.24 mmol) and potassium carbonate (169 mg, 1.22 mmol) were added and the mixture heated by microwave (250 W) at 100° C. for 20 minutes. The mixture was filtered through a cartridge, washing with DCM (5 mL) and the filtrate was evaporated to dryness and purified by mass-directed autopreparation. The appropriate fractions were evaporated, dissolved in DCM (10 mL), washed with aqueous sodium bicarbonate, and evaporated to give the title compound (32.7 mg).
LCMS: $t_{RET}$=3.17 min; MH⁺=268

Intermediate 10: 6-Methyl-1-phenyl-1H-indazol-4-amine

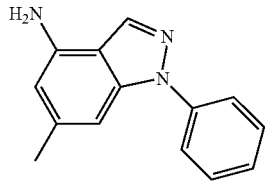

Similarly prepared to Intermediate 9 from 6-methyl-1H-indazol-4-amine and iodobenzene.
LCMS: $t_{RET}$=3.28 min; MH⁺=224

Intermediate 11: 1-(2,4-Difluorophenyl)-6-methyl-1H-indazol-4-amine

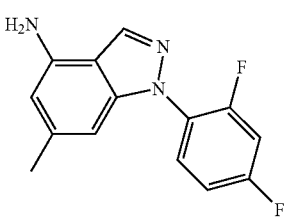

Similarly prepared to Intermediate 9 from 6-methyl-1H-indazol-4-amine and 2,4-difluoroiodobenzene.
LCMS: $t_{RET}$=3.22 min; MH⁺=260

Intermediate 12: 2,6-Dibromo-4-methylbenzaldehyde (2,4-difluorophenyl)hydrazone

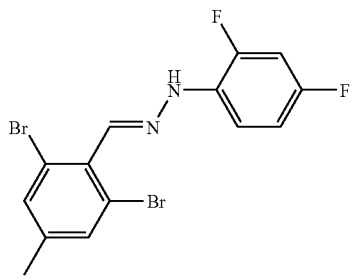

2,6-Dibromo-4-methylbenzaldehyde (89.5 g, 0.322 mol), (2,4-difluorophenyl)hydrazine hydrochloride (58.25 g, 0.322 mol) and sodium acetate (26.9 g, 0.328 mol) were heated in methanol (1.25 L) at reflux for 3.5 hours. The mixture was cooled and the precipitate was collected by filtration and partitioned between ethyl acetate (750 mL) and water (250 mL). The ethyl acetate layer was combined with a second ethyl acetate extract, washed successively with water and brine, dried over anhydrous sodium sulphate and evaporated under reduced pressure to afford the title compound as an off-white solid (97.5 g).

LCMS: $t_{RET}$=4.07 min; $MH^+$=403/405/407

Intermediate 13: 4-Bromo-1-(2,4-difluorophenyl)-6-methyl-1H-indazole

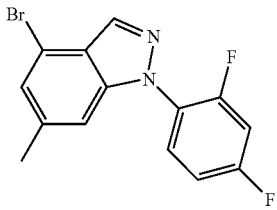

2,6-Dibromo-4-methylbenzaldehyde (2,4-difluorophenyl)hydrazone (Intermediate 12, 67.4 g, 0.167 mol), tripotassium phosphate (88.8 g, 0.418 mol), tris(dibenzylideneacetone)dipalladium(0) (3.4 g, 3.71 mmol) and racemic BINAP (2.09 g, 3.27 mmol) were heated in degassed 1,4-dioxane (1.125 L) under reflux for 4 days. The mixture was filtered through Celite, washing through with dichloromethane. The filtrate was evaporated under reduced pressure to give a dark brown residue which was dissolved in dichloromethane, absorbed onto silica gel, applied to a silica gel column (1 kg) and eluted with a gradient of 10 to 35% dichloromethane in hexane. Product containing fractions were combined and evaporated to give the title compound as a red solid (17.8 g).

$^1$H-NMR: (CDCl$_3$, 400 MHz) δ 8.18 (s, 1H), 7.57 (m, 1H), 7.25 (s, 1H), 7.02-7.13 (m, 3H), 2.47 (s, 3H)

Intermediate 14: 2,6-Dibromo-4-methylbenzaldehyde[4-(methyloxy)phenyl]hydrazone

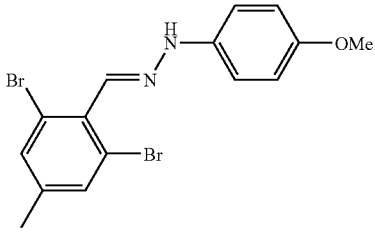

Sodium bicarbonate (0.84 g, 10 mmol) was added to a solution of 2,6-dibromo-4-methylbenzaldehyde (2.62 g, 9.43 mmol) and [4-(methyloxy)phenyl]hydrazine hydrochloride (1.65 g, 9.45 mmol) in methanol (60 mL) and the mixture heated under reflux for 15 min. The mixture was then cooled and evaporated to give the crude title compound which was used without purification.

LCMS: $t_{RET}$=3.97 min; $MH^+$=397/399/401

Intermediate 15: 4-Bromo-6-methyl-1-[4-(methyloxy)phenyl]-1H-indazole

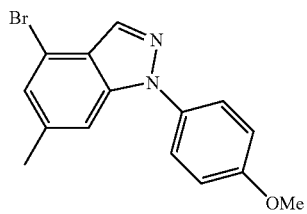

Crude 2,6-dibromo-4-methylbenzaldehyde[4-(methyloxy)phenyl]hydrazone (Intermediate 14 prepared from 2.62 g of 2,6-dibromo-4-methylbenzaldehyde) was dissolved in toluene (100 mL) and treated with tripotassium phosphate (5 g, 23.55 mmol), tris(dibenzylideneacetone)dipalladium(0) (196 mg, 0.214 mmol) and racemic BINAP (122 mg, 0.196 mmol). The mixture was heated under reflux for 17 hours and then cooled, filtered through celite and evaporated under reduced pressure. The residue was purified by silica gel chromatography using the Flashmaster II (100 g cartridge) eluting with a 100:0 to 0:100 cyclohexane:dichloromethane gradient over 60 minutes to give crude product (801 mg). Further purification by silica gel chromatography using the Flashmaster II (50 g cartridge) eluting with a 100:0 to 75:25 cyclohexane:ethyl acetate gradient over 50 minutes gave the title compound as a colourless solid (499 mg).

LCMS: $t_{RET}$=3.82 min; $MH^+$=317/319

Intermediate 16: 4-Bromo-6-methyl-1-[3-(methyloxy)phenyl]-1H-indazole

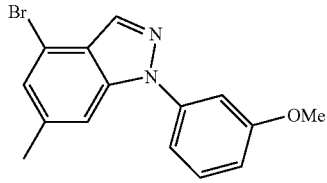

A mixture of 2,6-dibromo-4-methylbenzaldehyde (3.91 g, 14.07 mmol), sodium bicarbonate (1.2 g, 14.29 mmol) and [3-(methyloxy)phenyl]hydrazine hydrochloride (2.61 g, 14.95 mmol) was heated in methanol (125 mL) under reflux for 45 min. The mixture was cooled and evaporated under reduced pressure to give the crude intermediate hydrazone which was dried under reduced pressure for 1 hour and then dissolved in toluene (125 mL). Tripotassium phosphate (7.5 g, 35.33 mmol), tris(dibenzylideneacetone)dipalladium(0) (257 mg, 0.281 mmol) and racemic BINAP (175 mg, 0.281 mmol) were then added and the mixture heated under reflux under an atmosphere of nitrogen for 41 hours and then cooled.

The mixture was diluted with toluene (200 mL) and washed with water (2×150 mL). The aqueous phase was back extracted with ethyl acetate and the combined organic extracts were washed with brine (100 mL), dried over anhydrous sodium sulphate and evaporated under reduced pressure. The residue was purified by three sequential silica gel chromatography procedures using the Flashmaster II; Step 1 (2×70 g cartridges) eluting with a 100:0 to 50:50 cyclohexane:ethyl acetate gradient over 40 minutes, Step 2 (10 g cartridge) eluting with a 100:0 to 0:100 cyclohexane:dichloromethane gradient over 60 minutes, Step 3 (100 g cartridge) eluting with a 100:0 to 25:75 cyclohexane:dichloromethane gradient over 80 minutes to give the title compound (850 mg).

LCMS: $t_{RET}$=3.89 min; $MH^+$=317/319

Intermediate 17: 1,1,1-Trifluoro-4-[5-fluoro-2-(methyloxy)phenyl]-4-methyl-2-{[(phenylmethyl)amino]methyl}-2-pentanol

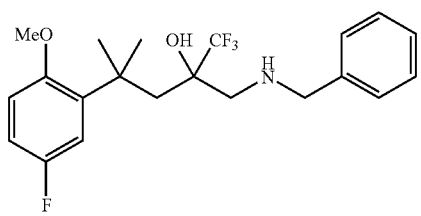

Benzylamine (38.6 mL, 0.353 mol) was added in one portion to a stirred solution of racemic 2-{2-[5-fluoro-2-(methyloxy)phenyl]-2-methylpropyl}-2-(trifluoromethyl)oxirane (which may be prepared according to WO 04/063163, 50 g, 0.171 mol) in ethanol (500 mL) at 20° C. and the resulting mixture heated at 80° C. overnight. The solvent was removed under reduced pressure and the resulting oil was purified by silica gel column chromatography eluting with 4% ethyl acetate in cyclohexane to give the title compound as a white solid (65.1 g).

LCMS: $t_{RET}$=2.83 min; $MH^+$=400

Intermediate 18: 2-(Aminomethyl)-1,1,1-trifluoro-4-[5-fluoro-2-(methyloxy)phenyl]-4-methyl-2-pentanol

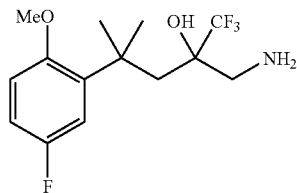

1,1,1-Trifluoro-4-[5-fluoro-2-(methyloxy)phenyl]-4-methyl-2-{[(phenylmethyl)amino]methyl}-2-pentanol (Intermediate 17, 63 g, 0.158 mol) was added to a stirred solution of 10% Pd/C (12.6 g, 50% wet) in ethanol (1.07 L) at 20° C. in a nitrogen purged vessel. The mixture was hydrogenated at 20° C. and atmospheric pressure until there was no further hydrogen uptake. The suspension was then filtered through Celite and glass fibre filter paper to remove the catalyst, and the cake washed with ethanol (120 mL). The combined filtrate and washings were evaporated under reduced pressure to give the title compound as a light grey solid (47.5 g).

LCMS: $t_{RET}$=2.37 min; $MH^+$=310

Intermediates 19 and 20: 1,1,1-Trifluoro-4-[5-fluoro-2-(methyloxy)phenyl]-4-methyl-2-({[(1R)-1-phenylethyl]amino}methyl)-2-pentanol

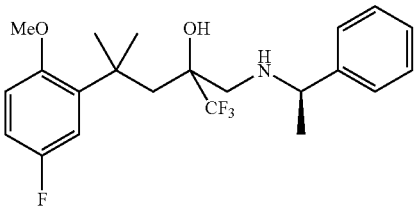

To a stirred solution of racemic 2-{2-[5-fluoro-2-(methyloxy)phenyl]-2-methylpropyl}-2-(trifluoromethyl)oxirane (600 mg, 2.05 mmol), which may be prepared according to WO04/063163, in anhydrous EtOH (3 mL) was added (R)-(+)-1-phenylethylamine (1.31 mL, 10.3 mmol). The reaction mixture was then stirred and heated at 50° C. under nitrogen for 5 days, cooled to room temperature and evaporated in vacuo. The residue was applied to a 70 g silica SPE cartridge and eluted with 0.5% $NH_3$ in toluene. The appropriate fractions were combined and evaporated in vacuo to give a colourless oil (991 mg). 710 mg of this oil was separated by chiral HPC on a 2 inch×15 cm Chiralpak AD column eluted with 25% acetonitrile/ammonium phosphate (pH 4.9) with a flow rate of 70 mL/min to give Intermediate 19 (2S isomer, 230 mg) after 17.5 min and Intermediate 20 (2R isomer, 200 mg) after 24.8 min.

Intermediate 19 (2S Isomer)

Single crystal X-ray structure on an orthorhombic crystal obtained by slow evaporation from ethyl acetate established the 2S configuration.

LCMS: $t_{RET}$=2.81 min; $MH^+$=414

Intermediate 20 (2R Isomer)

LCMS: $t_{RET}$=2.91 min; $MH^+$=414

Intermediate 21: (2R)-2-(Aminomethyl)-1,1,1-trifluoro-4-[5-fluoro-2-(methyloxy)phenyl]-4-methyl-2-pentanol

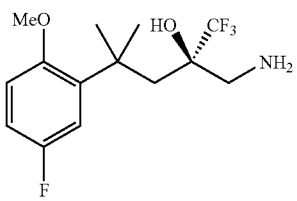

(2R)-1,1,1-Trifluoro-4-[5-fluoro-2-(methyloxy)phenyl]-4-methyl-2-({[(1R)-1-phenylethyl]amino}methyl)-2-pentanol (Intermediate 20) (200 mg, 0.48 mmol) was dissolved in EtOH (8 mL) and hydrogenated over 10% palladium on charcoal (100 mg) at 53 psi and room temperature for 16 hours. Catalyst was removed by filtration through celite. The celite was washed several times with EtOH. The filtrate was evaporated in vacuo to give the title compound as a pale yellow oil (158 mg).

LCMS: $t_{RET}$=2.38 min; MH$^+$=310

Intermediates 22 and 23: 4-(2,3-Dihydro-1-benzofuran-7-yl)-1,1,1-trifluoro-4-methyl-2-({[(1R)-1-phenylethyl]amino}methyl)-2-pentanol

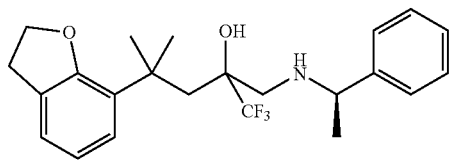

To an ice-cooled solution of (R)-(+)-1-phenylethylamine (4.43 mL, 34.9 mmol) in anhydrous EtOH (3 mL) was added, dropwise, racemic 7-{1,1-dimethyl-2-[2-(trifluoromethyl)-2-oxiranyl]ethyl}-2,3-dihydro-1-benzofuran (1 g, 3.49 mmol), which may be prepared according to WO04/063163. The reaction mixture was then heated at 50° C. overnight, cooled to room temperature and evaporated in vacuo. The residue was applied to a 50 g silica SPE cartridge and eluted with 0.5% NH$_3$ in toluene. The appropriate fractions were combined and evaporated in vacuo to give a colourless oil (1.486 g). This oil was subjected to mass-directed autopreparation to give Intermediate 22 (2S isomer, 314 mg), Intermediate 23 (2R isomer, 334 mg) plus a mixed fraction (480 mg). The mixed fraction was re-subjected to mass-directed auto-preparation to give further Intermediate 22 (90 mg), Intermediate 23 (125 mg) plus a mixed fraction (160 mg). The fractions containing Intermediate 22 were combined with each other as were the fractions containing Intermediate 23.

Intermediate 22 (2S isomer)

Single crystal X-ray structure on a triclinic crystal obtained by slow evaporation from isopropanol established the 2S configuration.

LCMS: $t_{RET}$=2.86 min; MH$^+$=408; melting point 65 to 68° C.

Intermediate 23 (2R isomer)

LCMS: $t_{RET}$=2.94 min; MH$^+$=408

Intermediate 24: (2R)-2-(Aminomethyl)-4-(2,3-dihydro-1-benzofuran-7-yl)-1,1,1-trifluoro-4-methyl-2-pentanol

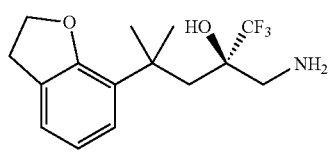

(2R)-4-(2,3-Dihydro-1-benzofuran-7-yl)-1,1,1-trifluoro-4-methyl-2-({[(1R)-1-phenylethyl]amino}methyl)-2-pentanol (Intermediate 23, (480 mg, 1.178 mmol) was dissolved in EtOH (13 mL) and hydrogenated over 10% palladium on charcoal (119 mg) at 50 psi and room temperature for 5 hours. Catalyst was removed by filtration through a microfibre filter pad and Celite. The Celite was washed several times with EtOH. The filtrate was evaporated in vacuo to give the title compound as a pale grey solid (330 mg).

LCMS: $t_{RET}$=2.43 min; MH$^+$=304

Intermediate 25: 2,6-Dibromo-4-methylbenzaldehyde (2-fluorophenyl)hydrazone

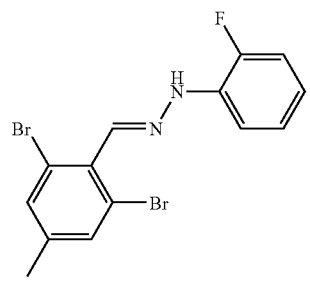

2,6-Dibromo-4-methylbenzaldehyde (600 g, 2.16 mmol), (2-fluorophenyl)hydrazine hydrochloride (351 mg, 2.16 mmol) and sodium acetate (180 mg, 2.19 mmol) were heated in methanol (15 mL) under reflux for 2 hours. The methanol was evaporated and the residue partitioned between dichloromethane (30 mL) and aqueous brine (30 mL). The organic phase was separated, combined with additional dichloromethane extracts (2×15 mL), washed with aqueous sodium bicarbonate (2×15 mL), passed through a hydrophobic frit and evaporated to the title compound (767 mg).

LCMS: $t_{RET}$=4.24 min; MH$^+$=387

Intermediate 26: 4-Bromo-1-(2-fluorophenyl)-6-methyl-1H-indazole

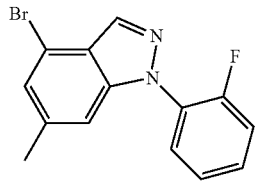

2,6-Dibromo-4-methylbenzaldehyde (2-fluorophenyl)hydrazone (Intermediate 25, 767 mg, 1.99 mmol), tripotassium phosphate (1.06 g, 4.98 mmol), tris(dibenzylideneacetone)dipalladium(0) (73 mg, 0.08 mmol) and racemic BINAP (50 mg, 0.08 mmol) were dissolved in toluene (26 mL) and heated under reflux for 16 hours in a nitrogen atmosphere. The mixture was then cooled and evaporated under reduced pressure. The residue purified by silica gel chromatography using the Flashmaster II (100 g cartridge) eluting with a 100:0 to 0:100 cyclohexane:dichloromethane gradient over 40 minutes to give the title compound (249 mg).

LCMS: $t_{RET}$=3.76 min; MH$^+$=305/307

Intermediate 27: 2.6-Dibromo-4-methylbenzaldehyde (4-fluorophenyl)hydrazone

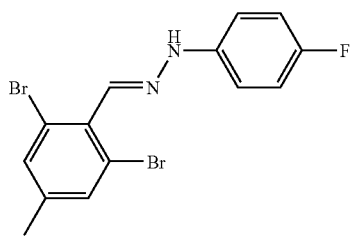

Similarly prepared to Intermediate 25 from 2,6-dibromo-4-methylbenzaldehyde and (4-fluorophenyl)hydrazine hydrochloride.

LCMS: $t_{RET}$=4.23 min; MH$^+$=387

Intermediate 28: 4-Bromo-1-(4-fluorophenyl)-6-methyl-1H-indazole

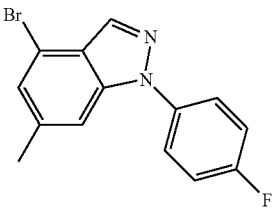

Similarly prepared to Intermediate 26 from 2,6-dibromo-4-methylbenzaldehyde (4-fluorophenyl)hydrazone (Intermediate 27).

LCMS: $t_{RET}$=3.90 min; MH$^+$=305/307

Intermediate 29: Phenylmethyl 3-(4-amino-6-methyl-1H-indazol-1-yl)benzoate

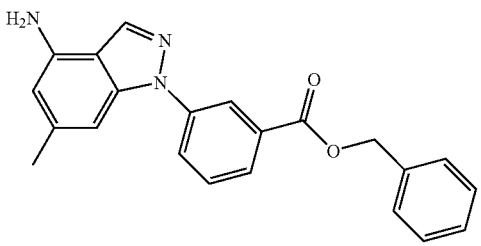

6-Methyl-1H-indazol-4-amine hydrochloride (0.5 g, 2.7 mmol), phenylmethyl 3-iodobenzoate (0.9 g, 2.6 mmol), copper (I) iodide (14 mg, 0.07 mmol), potassium carbonate (1.2 g, 8.68 mmol) and trans-N,N'-dimethyl-1,2-cyclohexanediamine (20 mg, 0.14 mmol) were heated together in DMF (5 mL) at reflux overnight. The mixture was cooled, poured into a mixture of water and ethyl acetate and filtered through celite. The organic phase was separated, combined with a second ethyl acetate extract, washed successively with water and brine and then dried over anhydrous sodium sulphate and evaporated under reduced pressure. The residue was purified by silica gel column chromatography (75 g) eluting with 1 to 5% gradient of ethyl acetate in dichloromethane to give the title compound (0.3 g).

$^1$H-NMR: (CDCl$_3$, 400 MHz) δ 8.46 (t, 1H), 8.10 (s, 1H), 8.06 (m, 1H), 7.96 (m, 1H), 7.61 (t, 1H), 7.49 (m, 2H), 7.42 (m, 2H), 7.38 (m, 1H), 6.96 (s, 1H), 6.31 (s, 1H), 5.44 (s, 2H), 4.15 (m, 2H), 2.42 (s, 3H)

Intermediate 30: Phenylmethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate

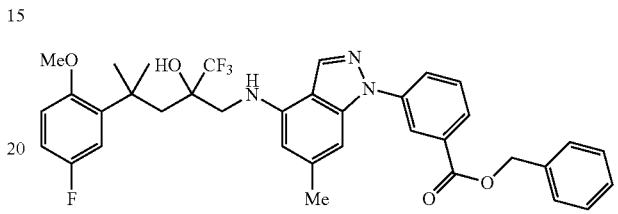

A mixture of racemic 2-{2-[5-fluoro-2-(methyloxy)phenyl]-2-methylpropyl}-2-(trifluoromethyl)oxirane (which may be prepared according to WO 04/063163, 350 mg, 1.2 mmol), phenylmethyl 3-(4-amino-6-methyl-1H-indazol-1-yl)benzoate (Intermediate 29, 357 mg, 1.0 mmol) and ytterbium(III) triflate (124 mg, 0.2 mmol) in acetonitrile (2 mL) was heated at 85° C. for 18 hours when the temperature was raised to reflux temperature and heating continued for a further 21 hours. The mixture was cooled to room temperature and partitioned between dichloromethane (50 mL) and aqueous sodium bicarbonate (50 mL). The aqueous layer was extracted again with dichloromethane (50 mL) and the combined organic extracts were dried over anhydrous sodium sulphate and evaporated. The residue was purified by silica gel chromatography using the Flashmaster II (50 g cartridge) eluting with a 1:1 cyclohexane:ethyl acetate gradient over 40 minutes to give the title compound as a white solid (424 mg).

$^1$H-NMR: (CDCl$_3$, 400 MHz) δ 8.40 (t, 1H), 8.04-8.07 (m, 1H), 7.97 (s, 1H), 7.91 (ddd, 1H), 7.60 (t, 1H), 7.46-7.49 (m, 2H), 7.35-7.43 (m, 4H), 7.17 (dd, 1H), 6.91-6.99 (m, 2H), 6.85 (dd, 1H), 5.70 (broad s, 1H), 5.42 (s, 2H), 3.87 (s, 3H), 3.35 (d, 1H), 3.12 (d, 1H), 2.88 (d, 1H), 2.38 (s, 3H), 2.28 (d, 1H), 1.46 (s, 3H), 1.43 (s, 3H)

Intermediate 31: (2S)-2-(Aminomethyl)-4-(2,3-dihydro-1-benzofuran-7-yl)-1,1,1-trifluoro-4-methyl-2-pentanol

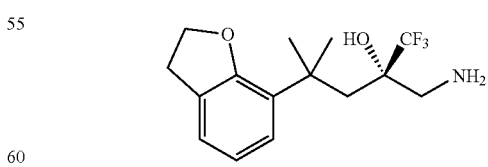

Similarly prepared to Intermediate 24 by hydrogenolysis of (2S)-4-(2,3-dihydro-1-benzofuran-7-yl)-1,1,1-trifluoro-4-methyl-2-({[(1R)-1-phenylethyl]amino}methyl)-2-pentanol (Intermediate 22).

LCMS: $t_{RET}$=2.40 min; MH$^+$=304

Intermediate 32: 2,6-Dibromo-4-methylbenzaldehyde phenylhydrazone

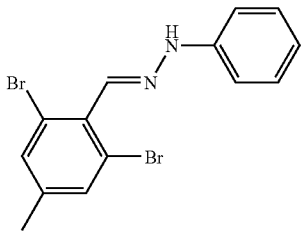

Similarly prepared to Intermediate 25 from 2,6-dibromo-4-methylbenzaldehyde and phenylhydrazine hydrochloride.
LCMS: $t_{RET}$=4.21 min; MH$^+$=369

Intermediate 33: 4-Bromo-6-methyl-1-phenyl-1H-indazole

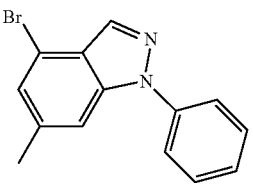

Similarly prepared to Intermediate 26 from 2,6-dibromo-4-methylbenzaldehyde phenylhydrazone (Intermediate 32).
LCMS: $t_{RET}$=3.90 min; MH$^+$=287/289

Example 1

1,1,1-Trifluoro-4-[5-fluoro-2-(methyloxy)phenyl]-2-({[1-(2-fluorophenyl)-1H-indazol-4-yl]amino}methyl)-4-methyl-2-pentanol

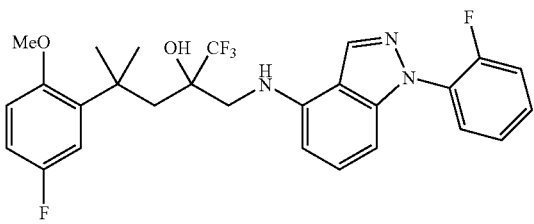

A mixture of racemic 2-{2-[5-fluoro-2-(methyloxy)phenyl]-2-methylpropyl}-2-(trifluoromethyl)oxirane (which may be prepared according to WO 04/063163, 29 mg, 0.1 mmol) and 1-(2-fluorophenyl)-1H-indazol-4-amine (Intermediate 1, 23 mg, 0.1 mmol) was heated by microwave (300 W) at 150° C. for 30 minutes. The crude product was cooled, dissolved in DMSO and purified by mass-directed autopreparation. The appropriate fractions were evaporated to give the title compound (7.2 mg).
LCMS: $t_{RET}$=4.01 min; MH$^+$=520

69 mg of similarly prepared racemic material was resolved by chiral HPLC on a 1 inch×25 cm Chiralcel OJ column eluted with heptane:EtOH 7:3 with a flow rate of 20 mL/min to provide Example 1-A (enantiomer A, 24 mg) and Example 1-B (enantiomer B, 26 mg)

Example 1-A (Enantiomer A)

Analytical chiral HPLC (25×0.46 cm Chiralcel OJ column, heptane:EtOH 7:3 eluting at 1 mL/min): $t_{RET}$=6.02 min
LCMS: $t_{RET}$=3.99 min; MH$^+$=520

Example 1-B (Enantiomer B)

Analytical chiral HPLC (25×0.46 cm Chiralcel OJ column, heptane:EtOH 7:3 eluting at 1 mL/min): $t_{RET}$=12.57 min
LCMS: $t_{RET}$=3.99 min; MH$^+$=520

Example 2

1,1,1-Trifluoro-4-[5-fluoro-2-(methyloxy)phenyl]-2-({[1-(4-fluorophenyl)-1H-indazol-4-yl]amino}methyl)-4-methyl-2-pentanol

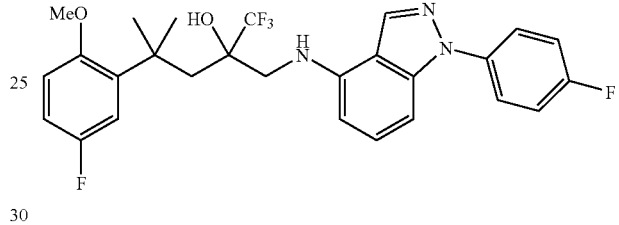

Prepared similarly to Example 1 from racemic 2-{2-[5-fluoro-2-(methyloxy)phenyl]-2-methylpropyl}-2-(trifluoromethyl)oxirane and 1-(4-fluorophenyl)-1H-indazol-4-amine (Intermediate 2).
LCMS: $t_{RET}$=4.10 min; MH$^+$=520

43 mg of this racemic material was resolved by chiral HPLC on a 25×2 cm Chiralcel OD column eluted with heptane:EtOH 7:3 with a flow rate of 15 mL/min to provide Example 2-A (enantiomer A, 13 mg) and Example 2-B (enantiomer B, 13 mg)

Example 2-A (Enantiomer A)

Analytical chiral HPLC (25×0.46 cm Chiralcel OD column, heptane:EtOH 7:3 eluting at 1 mL/min): $t_{RET}$=4.08 min
LCMS: $t_{RET}$=4.13 min; MH$^+$=520

Example 2-B (Enantiomer B)

Analytical chiral HPLC (25×46 cm Chiralcel OD column, heptane:EtOH 7:3 eluting at 1 mL/min): $t_{RET}$=6.09 min
LCMS: $t_{RET}$=4.13 min; MH$^+$=520

Example 3

1,1,1-Trifluoro-4-[5-fluoro-2-(methyloxy)phenyl-4-methyl-2-({1-[4-(methyloxy)phenyl]-1H-indazol-4-yl}amino)methyl]-2-pentanol

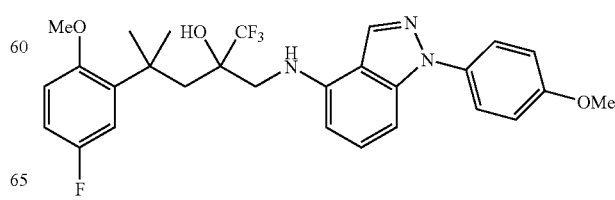

Prepared similarly to Example 1 from racemic 2-{2-[5-fluoro-2-(methyloxy)phenyl]-2-methylpropyl}-2-(trifluoromethyl)oxirane and 1-[4-(methyloxy)phenyl]-1H-indazol-4-amine (Intermediate 3).

LCMS: $t_{RET}$=3.94 min; MH$^+$=532

Example 4

2-({[1-(2,4-Difluorophenyl)-1H-indazol-4-yl]amino}methyl)-1,1'-trifluoro-4-[5-fluoro-2-(methyloxy)phenyl]-4-methyl-2-pentanol

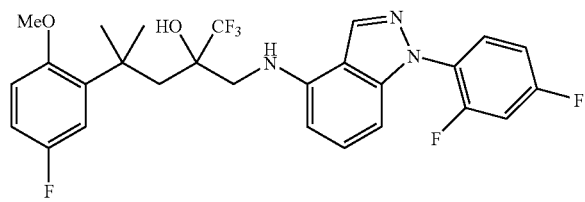

Prepared similarly to Example 1 from racemic 2-{2-[5-fluoro-2-(methyloxy)phenyl]-2-methylpropyl}-2-(trifluoromethyl)oxirane and 1-(2,4-difluorophenyl)-1H-indazol-4-amine (Intermediate 4).

LCMS: $t_{RET}$=3.94 min; MH$^+$=538

60 mg of this racemic material was resolved by chiral HPLC on a 1 inch×25 cm Chiralcel OD column eluted with heptane:EtOH 95:5 with a flow rate of 20 mL/min to provide Example 4-A (enantiomer A, 14 mg) and Example 4-B (enantiomer B, 12 mg)

Example 4-A (Enantiomer A)

Analytical chiral HPLC (25×0.46 cm Chiralcel OD-H column, heptane:EtOH 7:3 eluting at 1 mL/min): $t_{RET}$=3.99 min
LCMS: $t_{RET}$=4.03 min; MH$^+$=538

Example 4-B (Enantiomer B)

Analytical chiral HPLC (25×0.46 cm Chiralcel OD column, heptane:EtOH 7:3 eluting at 1 mL/min): $t_{RET}$=5.19 min
LCMS: $t_{RET}$=4.03 min; MH$^+$=538

Example 5

1,1,1-Trifluoro-4-[5-fluoro-2-(methyloxy)phenyl]-4-methyl-2-({[1-(4-pyridinyl)-1H-indazol-4-yl]amino}methyl)-2-pentanol

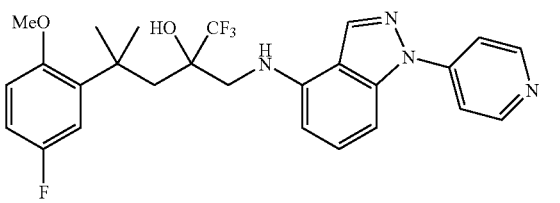

Prepared similarly to Example 1 from racemic 2-{2-[5-fluoro-2-(methyloxy)phenyl]-2-methylpropyl}-2-(trifluoromethyl)oxirane and 1-(4-pyridinyl)-1H-indazol-4-amine (Intermediate 5).

LCMS: $t_{RET}$=3.27 min; MH$^+$=503

Example 6

Ethyl 3-(4-{[4-[5-fluoro-2-(methyloxy)phenyl]-2-hydroxy-4-methyl-2-(trifluoromethyl)pentyl]amino}-1H-indazol-1-yl)benzoate

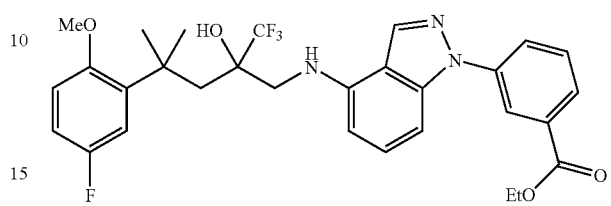

Prepared similarly to Example 1 from racemic 2-{2-[5-fluoro-2-(methyloxy)phenyl]-2-methylpropyl}-2-(trifluoromethyl)oxirane and ethyl 3-(4-amino-1H-indazol-1-yl)benzoate (Intermediate 6).

LCMS: $t_{RET}$=4.07 min; MH$^+$=574

42 mg of this racemic material was resolved by chiral HPLC on a 25×2 cm Chiralcel OD column eluted with heptane:EtOH 8:2 with a flow rate of 15 mL/min to provide Example 6-A (enantiomer A, 14 mg) and Example 6-B (enantiomer B, 14 mg)

Example 6-A (Enantiomer A)

Analytical chiral HPLC (25×0.46 cm Chiralcel OD-H column, heptane:EtOH 8:2 eluting at 1 mL/min): $t_{RET}$=5.73 min
LCMS: $t_{RET}$=4.25 min; MH$^+$=574

Example 6-B (Enantiomer B)

Analytical chiral HPLC (25×0.46 cm Chiralcel OD-H column, heptane:EtOH 8:2 eluting at 1 mL/min): $t_{RET}$=7.34 min
LCMS: $t_{RET}$=4.25 min; MH$^+$=574

Example 7

1,1,1-Trifluoro-4-[5-fluoro-2-(methyloxy)phenyl]-4-methyl-2-{[(1-phenyl-1H-indazol-4-yl)amino]methyl}-2-pentanol

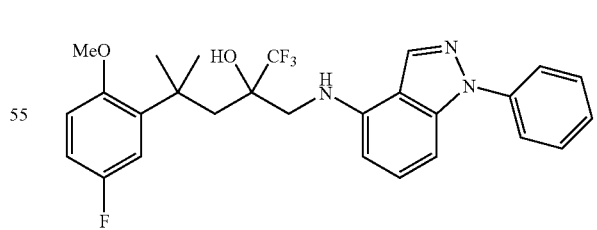

Prepared similarly to Example 1 from racemic 2-{2-[5-fluoro-2-(methyloxy)phenyl]-2-methylpropyl}-2-(trifluoromethyl)oxirane and 1-phenyl-1H-indazol-4-amine hydrochloride (as the free base, Intermediate 8) except that ca. 5 drops of NMP were added to the reaction mixture.

LCMS: $t_{RET}$=4.09 min; MH$^+$=502

Example 8

4-(2,3-Dihydro-1-benzofuran-7-yl)-1,1,1-trifluoro-4-methyl-2-{[(1-phenyl-1H-indazol-4-yl)amino]methyl}-2-pentanol

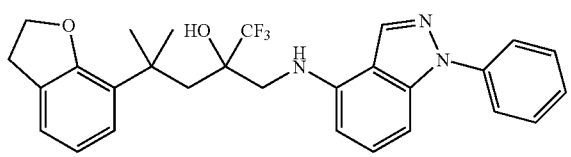

Prepared similarly to Example 7 from racemic 7-{1,1-dimethyl-2-[2-(trifluoromethyl)-2-oxiranyl]ethyl}-2,3-dihydro-1-benzofuran (which may be prepared according to WO 04/063163) and 1-phenyl-1H-indazol-4-amine hydrochloride (as the free base, Intermediate 8).
LCMS: $t_{RET}$=4.19 min; MH$^+$=496

Example 9

Ethyl 3-(4-{[4-(2,3-dihydro-1-benzofuran-7-yl)-2-hydroxy-4-methyl-2-(trifluoromethyl)pentyl]amino}-1H-indazol-1-yl)benzoate

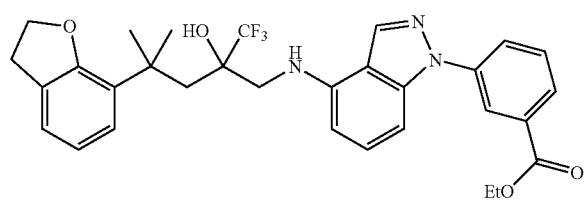

Prepared similarly to Example 1 from racemic 7-{1,1-dimethyl-2-[2-(trifluoromethyl)-2-oxiranyl]ethyl}-2,3-dihydro-1-benzofuran (which may be prepared according to WO 04/063163) and ethyl 3-(4-amino-1H-indazol-1-yl)benzoate (Intermediate 6).
LCMS: $t_{RET}$=4.17 min; MH$^+$=568

Example 10

4-(2,3-Dihydro-1-benzofuran-7-yl)-1,1,1-trifluoro-2-({[1-(2-fluorophenyl)-1H-indazol-4-yl]amino}methyl)-4-methyl-2-pentanol

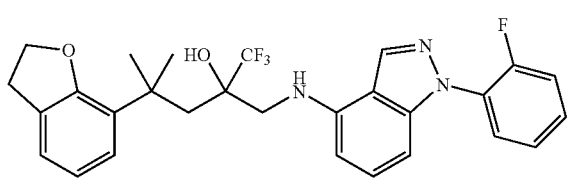

Prepared similarly to Example 1 from racemic 7-{1,1-dimethyl-2-[2-(trifluoromethyl)-2-oxiranyl]ethyl}-2,3-dihydro-1-benzofuran (which may be prepared according to WO 04/063163) and 1-(2-fluorophenyl)-1H-indazol-4-amine (Intermediate 1).
LCMS: $t_{RET}$=3.99 min; MH$^+$=514

Example 11

4-(2,3-Dihydro-1-benzofuran-7-yl)-1,1,1-trifluoro-2-({[1-(4-fluorophenyl)-1H-indazol-4-yl]amino}methyl)-4-methyl-2-pentanol

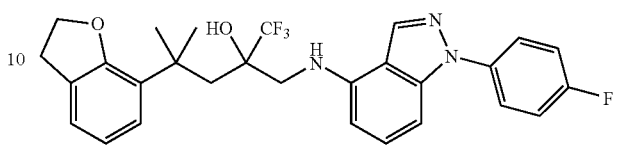

Prepared similarly to Example 1 from racemic 7-{1,1-dimethyl-2-[2-(trifluoromethyl)-2-oxiranyl]ethyl}-2,3-dihydro-1-benzofuran (which may be prepared according to WO 04/063163) and 1-(4-fluorophenyl)-1H-indazol-4-amine (Intermediate 2).
LCMS: $t_{RET}$=4.06 min; MH$^+$=514

Example 12

2-({[1-(2,4-Difluorophenyl)-1H-indazol-4-yl]amino}methyl)-4-(2,3-dihydro-1-benzofuran-7-yl)-1,1,1-trifluoro-4-methyl-2-pentanol

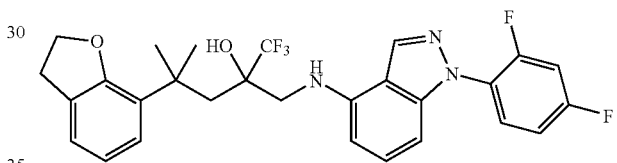

Prepared similarly to Example 1 from racemic 7-{1,1-dimethyl-2-[2-(trifluoromethyl)-2-oxiranyl]ethyl}-2,3-dihydro-1-benzofuran (which may be prepared according to WO 04/063163) and 1-(2,4-difluorophenyl)-1H-indazol-4-amine (Intermediate 4).
LCMS: $t_{RET}$=3.95 min; MH$^+$=532

Example 13

4-(2,3-Dihydro-1-benzofuran-7-yl)-1,1,1-trifluoro-4-methyl-2-({[1-(4-pyridinyl)-1H-indazol-4-yl]amino}methyl)-2-pentanol

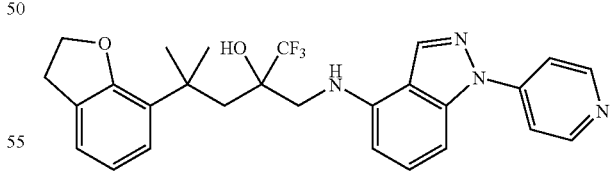

A mixture of racemic 7-{1,1-dimethyl-2-[2-(trifluoromethyl)-2-oxiranyl]ethyl}-2,3-dihydro-1-benzofuran (which may be prepared according to WO 04/063163, 27 mg, 0.095 mmol) and 1-(4-pyridinyl)-1H-indazol-4-amine (Intermediate 5) (20 mg, 0.095 mmol) was heated by microwave (200 W) at 150° C. for 20 minutes. The crude product was cooled, dissolved in DMSO/MeOH and purified by mass-directed autopreparation. The appropriate fractions were evaporated to give the title compound (4 mg).
LCMS: $t_{RET}$=3.59 min; MH$^+$=497

Example 14

Methyl 3-(4-{[4-[5-fluoro-2-(methyloxy)phenyl]-2-hydroxy-4-methyl-2-(trifluoro methyl)pentyl]amino}-1H-indazol-1-yl)benzoate

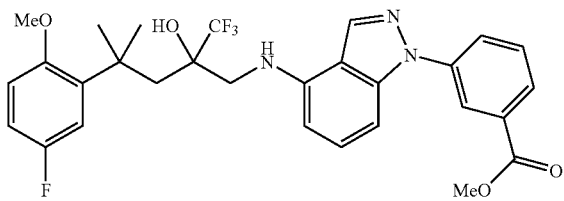

A mixture of racemic 2-{2-[5-fluoro-2-(methyloxy)phenyl]-2-methylpropyl}-2-(trifluoromethyl)oxirane (which may be prepared according to WO 04/063163, 35 mg, 0.12 mmol) and methyl 3-(4-amino-1H-indazol-1-yl)benzoate (Intermediate 9) (32.7 mg, 0.12 mmol) was heated by microwave (250 W) at 170° C. for 45 minutes. The crude product was cooled, dissolved in DMSO/MeOH and purified by mass-directed autopreparation. The appropriate fractions were evaporated, dissolved in DCM, washed with aqueous sodium bicarbonate, passed through a hydrophobic frit and evaporated to give the title compound (16.7 mg).

LCMS: $t_{RET}$=4.10 min; MH$^+$=560

40 mg of similarly prepared racemic material was resolved by chiral HPLC on a 2 inch×20 cm Chiralcel OD-H column eluted with heptane:EtOH 9:1 with a flow rate of 75 mL/min to provide Example 14-A (enantiomer A, 16 mg) and Example 14-B (enantiomer B, 10 mg)

Example 14-A (Enantiomer A)

Analytical chiral HPLC (25×0.46 cm Chiralcel OD-H column, heptane:EtOH 4:1 eluting at 1 mL/min): $t_{RET}$=6.28 min LCMS: $t_{RET}$=4.09 min; MH$^+$=560

Example 14-B (Enantiomer B)

Analytical chiral HPLC (25×0.46 cm Chiralcel OD-H column, heptane:EtOH 4:1 eluting at 1 mL/min): $t_{RET}$=7.92 min LCMS: $t_{RET}$=4.09 min; MH$^+$=560

Example 15

1,1,1-Trifluoro-4-[5-fluoro-2-(methyloxy)phenyl]-4-methyl-2-{[(6-methyl-1-phenyl-1H-indazol-4-yl)amino]methyl}-2-pentanol

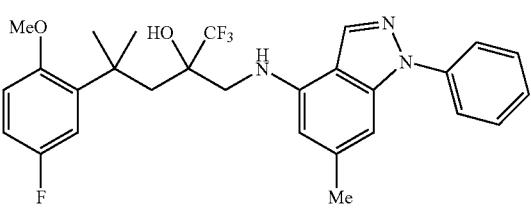

Prepared similarly to Example 14 from racemic 2-{2-[5-fluoro-2-(methyloxy)phenyl]-2-methylpropyl}-2-(trifluoromethyl)oxirane (which may be prepared according to WO 04/063163) and 6-methyl-1-phenyl-1H-indazol-4-amine (Intermediate 10).

LCMS: $t_{RET}$=4.20 min; MH$^+$=516

37 mg of this racemic material was resolved by chiral HPLC on a 25×2 cm Chiralcel OD column eluted with heptane:EtOH 4:1 with a flow rate of 15 mL/min to provide Example 15-A (enantiomer A, 9.4 mg) and Example 15-B (enantiomer B, 9.8 mg)

Example 15-A (Enantiomer A)

Analytical chiral HPLC (25×0.46 cm Chiralcel OD-H column, heptane:EtOH 4:1 eluting at 1 mL/min): $t_{RET}$=5.50 min LCMS: $t_{RET}$=4.13 min; MH$^+$=516

Example 15-B (Enantiomer B)

Analytical chiral HPLC (25×0.46 cm Chiralcel OD-H column, heptane:EtOH 4:1 eluting at 1 mL/min): $t_{RET}$=6.64 min LCMS: $t_{RET}$=4.15 min; MH$^+$=516

Example 16

2-({[1-(2,4-Difluorophenyl)-6-methyl-1H-indazol-4-yl]amino}methyl)-1,1,1-trifluoro-4-[5-fluoro-2-(methyloxy)phenyl]-4-methyl-2-pentanol

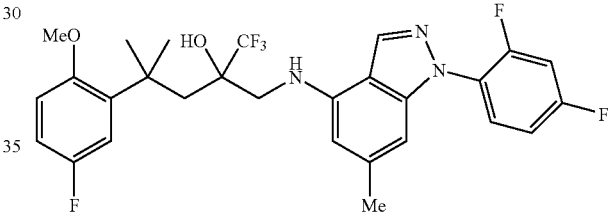

Method A

A mixture of racemic 2-{2-[5-fluoro-2-(methyloxy)phenyl]-2-methylpropyl}-2-(trifluoromethyl)oxirane (which may be prepared according to WO 04/063163, 53 mg, 0.18 mmol) and 1-(2,4-difluorophenyl)-6-methyl-1H-indazol-4-amine (Intermediate 11, 47 mg, 0.18 mmol) was heated by microwave (250 W) at 170° C. for 45 minutes and then at 300 W and 170° C. for a further 45 minutes. The mixture was cooled, diluted with DMSO/MeOH (1:1) and purified by mass-directed autopreparation. A second reaction was conducted on the same scale, heating by microwave at 300 W at 170° C. for 45 minutes and purified in the same manner. The appropriate fractions from the two reactions were combined, neutralised with aqueous sodium bicarbonate (50 mL) and extracted with DCM (×2). The combined DCM extracts were dried over anhydrous sodium sulphate and evaporated to give the title compound (32.1 mg).

LCMS: $t_{RET}$=4.17 min; MH$^+$=552

26 mg of this racemic material was resolved by chiral HPLC on a 25×2 cm Chiralpak AD column eluted with heptane:EtOH 4:6 with a flow rate of 15 mL/min to provide Example 16-A (enantiomer A, 9.2 mg) and Example 16-B (enantiomer B, 9.2 mg)

Example 16-A (Enantiomer A, 2R Isomer)

Analytical chiral HPLC (25×0.46 cm Chiralpak AD column, heptane:EtOH 4:6 eluting at 1 mL/min): $t_{RET}$=6.1 min LCMS: $t_{RET}$=4.17 min; MH$^+$=552

Example 16-B (Enantiomer B, 2S Isomer)

Analytical chiral HPLC (25×0.46 cm Chiralpak AD column, heptane:EtOH 4:6 eluting at 1 mL/min): $t_{RET}$=11.0 min LCMS: $t_{RET}$=4.16 min; MH$^+$=552

Method B

To a stirred solution of 4-bromo-1-(2,4-difluorophenyl)-6-methyl-1H-indazole (Intermediate 13, 13.4 g, 41.47 mmol) in toluene (95 mL) at 20° C. under nitrogen were successively added 2-(aminomethyl)-1,1,1-trifluoro-4-[5-fluoro-2-(methyloxy)phenyl]-4-methyl-2-pentanol (Intermediate 18, 14.1 g, 45.58 mmol), tris(dibenzylideneacetone)dipalladium(0) (3.7 g, 4.04 mmol), racemic-BINAP (2.5 g, 4.01 mmol) and sodium tert-butoxide (5.6 g, 58.27 mmol). The mixture was heated to 110° C. for 3 hours, and then allowed to cool to 20° C. The reaction mixture was then poured into ethyl acetate (200 mL), and filtered through Celite. The cake was washed with ethyl acetate (50 mL) and the combined ethyl acetate phases were evaporated under reduced pressure. The residue was purified by column chromatography eluting with 20% ethyl acetate in cyclohexane to afford the title compound as a light brown solid (15.0 g).

LCMS: LCMS: $t_{RET}$=4.16 min; MH$^+$=552

Example 16-A (2R)-2-({[1-(2,4-Difluorophenyl)-6-methyl-1H-indazol-4-yl]amino}methyl)-1,1,1-trifluoro-4-[5-fluoro-2-(methyloxy)phenyl]-4-methyl-2-Pentanol

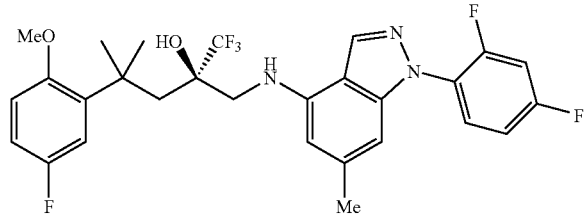

A solution of (2R)-2-(aminomethyl)-1,1,1-trifluoro-4-[5-fluoro-2-(methyloxy)phenyl]-4-methyl-2-pentanol (Intermediate 21, 20 mg, 0.065 mmol), 4-bromo-1-(2,4-difluorophenyl)-6-methyl-1H-indazole (Intermediate 13, 18.3 mg, 0.057 mmol), tris(dibenzylideneacetone)dipalladium(0) (2.6 mg, 0.0028 mmol), racemic-BINAP (3.6 mg, 0.0056 mmol) and sodium tert-butoxide (7.7 mg, 0.081 mmol) in toluene (0.4 mL) was heated in a microwave at 120° C. for 15 min. The mixture was then cooled, partitioned between ethyl acetate (20 mL) and aqueous ammonium chloride (20 mL). The organic layer was separated, washed successively with aqueous sodium bicarbonate, water and brine, passed through a hydrophobic frit and evaporated. The residue was purified by mass-directed autopreparation to give the title compound (6.5 mg).

LCMS: $t_{RET}$=4.16 min; MH$^+$=552. Analytical chiral HPLC (25×0.46 cm Chiralpak AD column, heptane:EtOH 4:6 eluting at 1 mL/min): $t_{RET}$=6.1 min.

Example 17

4-(2,3-Dihydro-1-benzofuran-7-yl)-1,1,1-trifluoro-4-methyl-2-{[(6-methyl-1-phenyl-1H-indazol-4-yl)amino]methyl}-2-pentanol

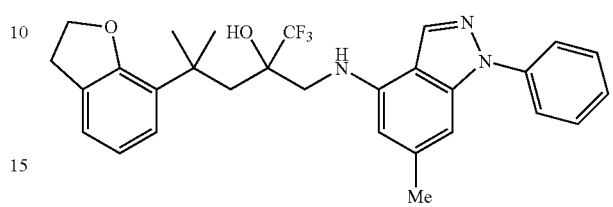

Prepared similarly to Example 14 from racemic 7-{1,1-dimethyl-2-[2-(trifluoromethyl)-2-oxiranyl]ethyl}-2,3-dihydro-1-benzofuran (which may be prepared according to WO 04/063163) and 6-methyl-1-phenyl-1H-indazol-4-amine (Intermediate 10).

LCMS: $t_{RET}$=4.17 min; MH$^+$=510. Analytical chiral HPLC (25×0.46 cm Chiralcel OD-H column, heptane:EtOH 95:5 eluting at 1 mL/min): $t_{RET}$=14.2 min and 17.7 min.

Example 17-A (2S)-4-(2,3-Dihydro-1-benzofuran-7-yl)-1,1,1-trifluoro-4-methyl-2-{[(6-methyl-1-phenyl-1H-indazol-4-yl)amino]methyl}-2-pentanol

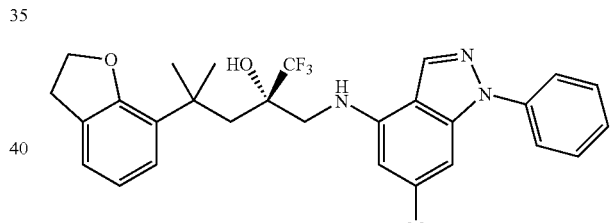

To a mixture of (2S)-2-(aminomethyl)-4-(2,3-dihydro-1-benzofuran-7-yl)-1,1,1-trifluoro-4-methyl-2-pentanol (Intermediate 31, 87 mg, 0.3 mmol) and 4-bromo-6-methyl-1-phenyl-1H-indazole (Intermediate 33, 92 mg, 0.32 mmol) in toluene (3.5 mL) were added tris(dibenzylideneacetone)dipalladium(0) (35 mg, 0.04 mmol), racemic-BINAP (28 mg, 0.04 mmol) and sodium tert-butoxide (45 mg, 0.47 mmol). The mixture was heated in a microwave at 120° C. for 15 min and then cooled and partitioned between ethyl acetate (30 mL) and water (20 mL). The organic layer was separated, washed with water (20 mL), passed through a hydrophobic frit and evaporated. The residue was purified by two sequential SPE cartridge purifications eluting with a gradient of ethyl acetate:petroleum:ether (1:6 to 1:4) to give the title compound as a yellow foam (43 mg).

LCMS: $t_{RET}$=4.06 min; MH$^+$=510. Analytical chiral HPLC (25×0.46 cm Chiralcel OD-H column, heptane:EtOH 95:5 eluting at 1 mL/min): $t_{RET}$=13.9 min (93%).

Example 17-B (2R)-4-(2,3-Dihydro-1-benzofuran-7-yl)-1,1,1-trifluoro-4-methyl-2-{[(6-methyl-1-phenyl-1H-indazol-4-yl)amino]methyl}-2-pentanol

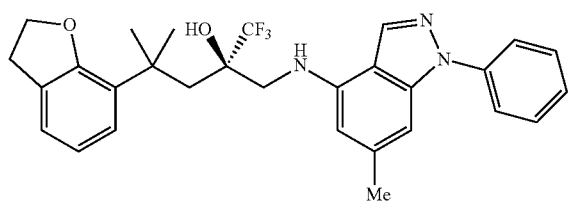

Prepared similarly to Example 17-A from (2R)-2-(aminomethyl)-4-(2,3-dihydro-1-benzofuran-7-yl)-1,1,1-trifluoro-4-methyl-2-pentanol (Intermediate 24) and 4-bromo-6-methyl-1-phenyl-1H-indazole (Intermediate 33).

LCMS: $t_{RET}$=4.08 min; MH$^+$=510. Analytical chiral HPLC (25×0.46 cm Chiralcel OD-H column, heptane:EtOH 95:5 eluting at 1 mL/min): $t_{RET}$=17.2 min (97.3%).

Example 18

2(R)-2-[3-({[1-(2,4-Difluorophenyl)-6-methyl-1H-indazol-4-yl]amino}methyl)-4,4,4-trifluoro-3-hydroxy-1,1-dimethylbutyl]-4-fluorophenol

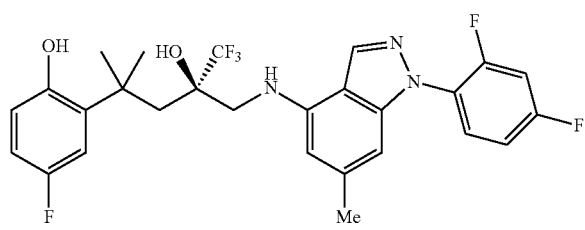

Method A (2R)-2-({[1-(2,4-Difluorophenyl)-6-methyl-1H-indazol-4-yl]amino}methyl)-1,1,1-trifluoro-4-[5-fluoro-2-(methyloxy)phenyl]-4-methyl-2-pentanol (Example 16-A, 325 mg, 0.59 mmol) was dissolved in anhydrous dichloromethane (1 mL) and cooled to −78° C. (cardice/acetone bath) under nitrogen. Boron tribromide (1.0M in dichloromethane) (4.9 mL, 4.9 mmol) was then added portionwise and after 5 minutes the mixture was allowed to warm to room temperature. The reaction was stirred at room temperature for 23 hours, re-cooled to −78° C. and quenched with methanol (3 mL). The reaction was warmed to room temperature, partitioned between dichloromethane (20 mL) and aqueous saturated sodium hydrogen carbonate solution (20 mL), poured onto a hydrophobic frit and the dichloromethane layer collected and evaporated in vacuo to yield crude material. The crude product was purified by mass-directed autopreparation. The appropriate fractions were neutralised using aqueous sodium hydrogen carbonate solution and extracted into dichloromethane. The organic layer was separated and the aqueous phase was back-extracted with further dichloromethane. The combined organic layers were washed with aqueous sodium hydrogen carbonate solution followed by water and then brine, filtered through a hydrophobic frit and evaporated in vacuo to give the title compound (112 mg).

LCMS: $t_{RET}$=3.89 min; MH$^+$=538

Method B

Boron tribromide (1 M in dichloromethane) (250 mL, 250 mmol) was added over 30 min to a stirred solution of (2R)-2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol (Example 16-A, 14.0 g, 25.4 mmol) in dichloromethane (125 mL) at −78° C. under nitrogen. The mixture was allowed to warm to 20° C., and was stirred for 5 days. The mixture was then cooled to −78° C. and methanol (200 mL) was added. The reaction mixture was allowed to warm up to 20° C., and was washed consecutively with water (280 mL) and saturated sodium bicarbonate (200 mL) and evaporated under reduced pressure. The residual solid was dissolved in methanol (1 L), filtered through a glass fibre filter and evaporated under reduced pressure. The residual solid was triturated with methanol (30 mL) at 40° C. and collected by filtration, washed with methanol (60 mL) and dried in vacuo at 40° C. overnight to afford the title compound as a beige solid (11.0 g).

LCMS: LCMS: $t_{RET}$=3.99 min; MH$^+$=538, $^1$H-NMR: (DMSO-d$_6$, 400 MHz) δ 9.77 (s, 1H), 8.20 (d, J=1.0 Hz, 1H), 7.64 (m, 1H), 7.59 (m, 1H), 7.29 (m, 1H), 7.02 (dd, J=11.0, 3.0 Hz, 1H), 6.90 (td, J=8.5, 3.0 Hz, 1H), 6.83 (dd, J=8.5, 5.0 Hz, 1H), 6.27 (m, 1H), 5.93 (s, 1H), 5.46 (m, 2H), 3.19 (d, J=14.5 Hz, 1H), 3.10 (dd, J=13.5, 2.5 Hz, 1H), 2.90 (dd, J=13.5, 7.0 Hz, 1H), 2.22 (s, 3H), 1.91 (d, J=14.5 Hz, 1H), 1.56 (s, 3H), 1.39 (s, 3H)

Example 19

1,1,1-Trifluoro-4-[5-fluoro-2-(methyloxy)phenyl]-4-methyl-2-[({6-methyl-1-[4-(methyloxy)phenyl]-1H-indazol-4-yl}amino)methyl]-2-pentanol

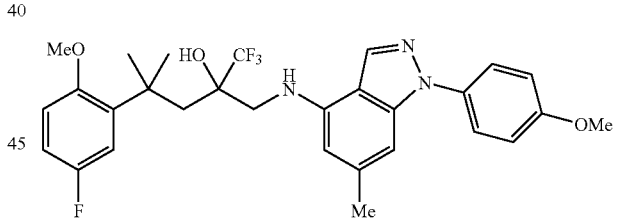

To a mixture of 2-(aminomethyl)-1,1,1-trifluoro-4-[5-fluoro-2-(methyloxy)phenyl]-4-methyl-2-pentanol (Intermediate 18, 200 mg, 0.65 mmol) and 4-bromo-6-methyl-1-[4-(methyloxy)phenyl]-1H-indazole (Intermediate 15, 190 mg, 0.6 mmol) in toluene (3 mL) were added tris(dibenzylideneacetone)dipalladium(0) (28 mg, 0.03 mmol), racemic-BINAP (37 mg, 0.06 mmol) and sodium tert-butoxide (85 mg, 0.84 mmol). The mixture was heated in a microwave at 120° C. for 30 min and then cooled and partitioned between ethyl acetate (60 mL) and 1M hydrochloric acid (60 mL). The organic layer was separated, washed sequentially with aqueous sodium bicarbonate (30 mL) and brine (30 mL), passed through a hydrophobic frit and evaporated under reduced pressure. The residue was dissolved in dichloromethane (1.5 mL) and loaded onto a silica SPE cartridge and eluted with a gradient of ethyl acetate:petroleum ether (1:9 to 1:4) to give the title compound (194 mg).

LCMS: $t_{RET}$=4.05 min; MH$^+$=545

Example 20

4-(4-{[4-[5-Fluoro-2-(methyloxy)phenyl]-2-hydroxy-4-methyl-2-(trifluoromethyl)pentyl]amino}-6-methyl-1H-indazol-1-yl)phenol and Example 21: 4-Fluoro-2-[4,4,4-trifluoro-3-hydroxy-3-({[1-(4-hydroxyphenyl)-6-methyl-1H-indazol-4-yl]amino}methyl)-1,1-dimethylbutyl]phenol

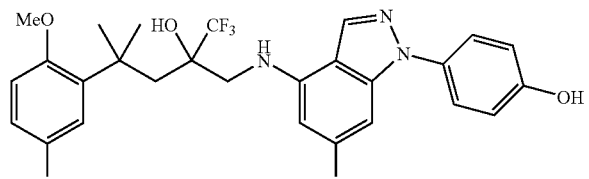

Example 20

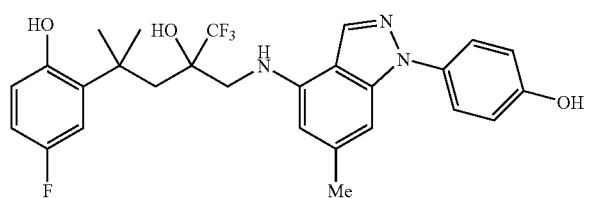

Example 21

1,1,1-Trifluoro-4-[5-fluoro-2-(methyloxy)phenyl]-4-methyl-2-[({6-methyl-1-[4-(methyloxy)phenyl]-1H-indazol-4-yl}amino)methyl]-2-pentanol (Example 19, 38 mg, 0.07 mmol) was dissolved in anhydrous dichloromethane (8 ml) and cooled to −78° C. (cardice/acetone bath). Boron tribromide (1.0M in dichloromethane, 0.15 ml, 0.15 mmol) was added and the mixture allowed to warm to room temperature over 2 hours and then stirred for a further 21 hours. The mixture was cooled to −70° C. when more boron tribromide (1.0M in dichloromethane, 0.1 ml, 0.1 mmol) was added and the mixture was allowed to warm to room temperature and stirred for a further 3 hours. The mixture was then diluted with dichloromethane (20 mL), cooled in ice and quenched with methanol (3 ml). After a further 5 min more dichloromethane (15 mL) was added and the solution washed with aqueous sodium hydrogen carbonate solution (2×20 ml), passed through a hydrophobic frit and evaporated under reduced pressure to yield crude material. This crude product was purified by mass-directed autopreparation to give Example 20 (12 mg), LCMS: $t_{RET}$=3.92 min; MH$^+$=532, and Example 21 (13 mg). LCMS: $t_{RET}$=3.72 min; MH$^+$=518

Example 22

1,1,1-Trifluoro-4-[5-fluoro-2-(methyloxy)phenyl]-4-methyl-2-[({6-methyl-1-[3-(methyloxy)phenyl]-1H-indazol-4-yl}amino)methyl]-2-pentanol

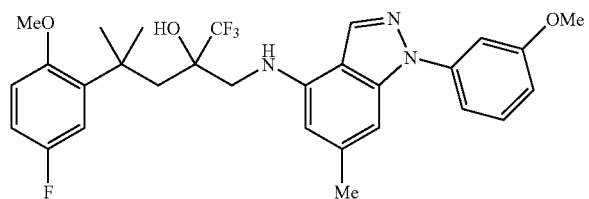

A mixture of 2-(aminomethyl)-1,1,1-trifluoro-4-[5-fluoro-2-(methyloxy)phenyl]-4-methyl-2-pentanol (Intermediate 18, 743 mg, 2.4 mmol), 4-bromo-6-methyl-1-[3-(methyloxy)phenyl]-1H-indazole (Intermediate 16, 657 mg, 2.07 mmol), tris(dibenzylideneacetone)dipalladium(0) (117 mg, 0.13 mmol), racemic-BINAP (141 mg, 0.23 mmol) and sodium tert-butoxide (429 mg, 4.46 mmol) in toluene (30 mL) was heated under reflux in an atmosphere of nitrogen for 2 hours. The mixture was cooled, combined with crude product from a similar smaller scale preparation (260 mg input of Intermediate 18), and diluted with toluene (100 mL) and ethyl acetate (50 mL). The resulting solution was washed successively with 1M hydrochloric acid (75 mL), 8% aqueous sodium bicarbonate (75 mL) and brine (75 mL), passed through a hydrophobic frit and evaporated under reduced pressure. The residue was purified by silica gel chromatography using the Flashmaster II (70 g cartridge) eluting with a 0:100 to 50:50 cyclohexane:ethyl acetate gradient over 60 minutes to give impure product (970 mg). Further purification using the Flashmaster II (100 g cartridge) eluting with a 100:0 to 75:25 dichloromethane:tert-butyl methyl ether gradient over 50 minutes gave the title compound (72 mg). A quantity of less pure material (137 mg) was also obtained.

$^1$H-NMR: (CDCl$_3$, 400 MHz) δ 7.91 (s, 1H), 7.41 (t, 1H), 7.22-7.29 (m, 2H), 7.18 (dd, 1H), 6.97 (ddd, 1H), 6.94 (broad s, 1H), 6.88-6.92 (m, 2H), 6.86 (dd, 1H), 5.61 (s, 1H), 4.08 (dd, 1H), 3.88 (s, 3H), 3.87 (s, 3H), 3.34 (dd, 1H), 3.10 (dd, 1H), 2.90 (d, 1H), 2.38 (s, 3H), 2.26 (d, 1H), 1.46 (s, 3H), 1.20 (s, 3H)

Example 23

3-(4-{[4-[5-Fluoro-2-(methyloxy)phenyl]-2-hydroxy-4-methyl-2-(trifluoromethyl)pentyl]amino}-6-methyl-1H-indazol-1-yl)phenol

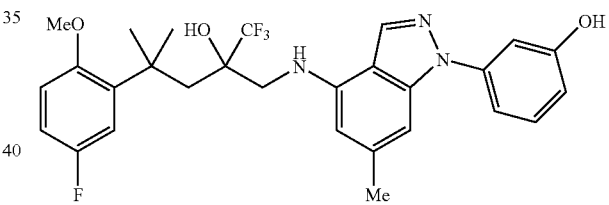

1,1,1-Trifluoro-4-[5-fluoro-2-(methyloxy)phenyl]-4-methyl-2-[({6-methyl-1-[3-(methyloxy)phenyl]-1H-indazol-4-yl}amino)methyl]-2-pentanol (Example 22, 46 mg, 0.085 mmol) was dissolved in anhydrous dichloromethane (4 ml) and cooled to −70° C. (cardice/acetone bath). Boron tribromide (1.0M in dichloromethane, 0.15 ml, 0.15 mmol) was added and the mixture allowed to warm to room temperature over 2 hours and then stirred for a further 20 hours. The mixture was cooled to −70° C. and more boron tribromide (1.0M in dichloromethane, 0.1 ml, 0.1 mmol) was added and the mixture was allowed to warm to room temperature and stirred for a further 20 hours. The mixture was cooled again to −70° C. and more boron tribromide (1.0M in dichloromethane, 0.1 ml, 0.1 mmol) was added and the mixture was allowed to warm to room temperature and stirred for a further 32 hours. The mixture was then diluted with dichloromethane (15 mL), cooled in ice and quenched with methanol (3 mL). After a further 15 min the mixture was partitioned between dichloromethane (35 mL) and aqueous sodium bicarbonate (35 mL). The organic phase was washed again with aqueous sodium bicarbonate (35 mL), passed through a hydrophobic frit and evaporated under reduced pressure to yield crude material. This crude product was purified by mass-directed autopreparation to give the title compound (9 mg).

LCMS: $t_{RET}$=3.90 min; MH$^+$=532

Example 24

4-Fluoro-2-[4,4,4-trifluoro-3-hydroxy-3-({[1-(3-hydroxyphenyl)-6-methyl-1H-indazol-4-yl]amino}methyl)-1,1-dimethylbutyl]phenol

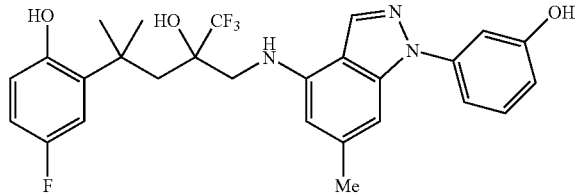

A mixture of 1,1,1-trifluoro-4-[5-fluoro-2-(methyloxy)phenyl]-4-methyl-2-[({6-methyl-1-[3-(methyloxy)phenyl]-1H-indazol-4-yl}amino)methyl]-2-pentanol (Example 22, 137 mg, 0.25 mmol) and lithium iodide (1 g, 7.5 mmol) in N-methylpyrrolidinone (6 mL) was heated in a microwave at 220° C. for 55 minutes. The solvent was removed using a vacuum centrifuge and the residue was partitioned between water (25 mL) and dichloromethane (50 mL) and passed through a hydrophobic frit. The organic filtrate was evaporated under reduced pressure and purified by silica gel chromatography (20 g cartridge) eluting with a 100:0 to 0:100 gradient of cyclohexane:ethyl acetate over 30 minutes to give the title compound (41 mg).

LCMS: $t_{RET}$=3.70 min; MH$^+$=518

9 mg of similarly prepared racemic material was resolved by chiral HPLC on a 25×2 cm Chiralpak AD column eluted with heptane:EtOH 3:1 with a flow rate of 15 mL/min to provide Example 24-A (enantiomer A, 1.4 mg) and Example 24-B (enantiomer B, 1.5 mg)

Example 24-A (Enantiomer A)

Analytical chiral HPLC (25×0.46 cm Chiralpak AD column, heptane:EtOH 3:1 eluting at 1 mL/min): $t_{RET}$=9.54 min
LCMS: $t_{RET}$=3.89 min; MH$^+$=518

Example 24-B (Enantiomer B)

Analytical chiral HPLC (25×0.46 cm Chiralpak AD column, heptane:EtOH 3:1 eluting at 1 mL/min): $t_{RET}$=13.77 min
LCMS: $t_{RET}$=3.90 min; MH$^+$=518

Example 25

1,1,1-Trifluoro-4-[5-fluoro-2-(methyloxy)phenyl]-2-({[1-(2-fluorophenyl)-6-methyl-1H-indazol-4-yl]amino}methyl)-4-methyl-2-pentanol

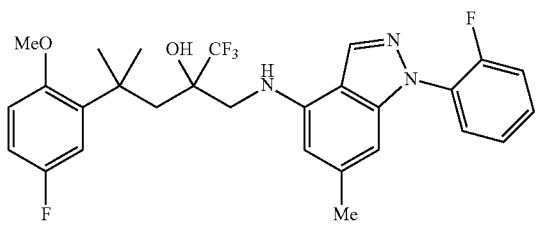

To a mixture of 2-(aminomethyl)-1,1,1-trifluoro-4-[5-fluoro-2-(methyloxy)phenyl]-4-methyl-2-pentanol (Intermediate 18, 49.5 mg, 0.16 mmol) and 4-bromo-1-(2-fluorophenyl)-6-methyl-1H-indazole (Intermediate 26, 45.8 mg, 0.15 mmol) in toluene (0.75 mL) were added tris(dibenzylideneacetone)dipalladium(0) (6.9 mg, 0.075 mmol), racemic-BINAP (9.3 mg, 0.015 mmol) and sodium tert-butoxide (18.5 mg, 0.192 mmol). The mixture was heated in a microwave at 120° C. for 30 min and then cooled and partitioned between water and dichloromethane. The organic layer was separated, dried and purified by silica gel chromatography using the Flashmaster II (20 g cartridge) eluting with a 0:100 cyclohexane:ethyl acetate gradient over 60 minutes to give crude product (43.6 mg) which was purified further by mass-directed autopreparation to give the title compound (18 mg).

LCMS: $t_{RET}$=4.14 min; MH$^+$=534

This racemic material was resolved by chiral HPLC on a 25×2 cm Chiralcel OJ column eluted with heptane:EtOH 7:3 with a flow rate of 15 mL/min to provide Example 25-A (enantiomer A, 7.0 mg) and Example 25-B (enantiomer B, 7.4 mg)

Example 25-A (Enantiomer A)

Analytical chiral HPLC (25×0.46 cm Chiralcel OJ column, heptane:EtOH 7:3 eluting at 1 mL/min): $t_{RET}$=7.4 min
LCMS: $t_{RET}$=4.14 min; MH$^+$=534

Example 25-B (Enantiomer B)

Analytical chiral HPLC (25×0.46 cm Chiralcel OJ column, heptane:EtOH 7:3 eluting at 1 mL/min): $t_{RET}$=14.1 min
LCMS: $t_{RET}$=4.14 min; MH$^+$=534

Example 26

1,1,1-Trifluoro-4-[5-fluoro-2-(methyloxy)phenyl]-2-({[1-(4-fluorophenyl)-6-methyl-1H-indazol-4-yl]amino}methyl)-4-methyl-2-pentanol

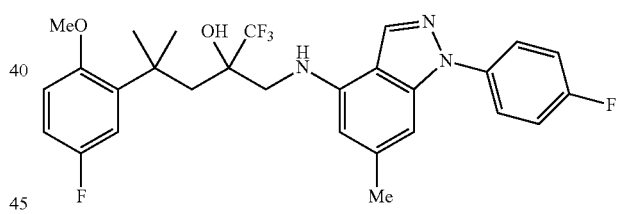

Prepared similarly to Example 25 from 2-(aminomethyl)-1,1,1-trifluoro-4-[5-fluoro-2-(methyloxy)phenyl]-4-methyl-2-pentanol (Intermediate 18) and 4-bromo-1-(4-fluorophenyl)-6-methyl-1H-indazole (Intermediate 28). Purification was conducted by silica gel chromatography using the Flashmaster II (20 g cartridge) eluting with a 100:0 to 50:50 cyclohexane:ethyl acetate gradient over 40 minutes to give the title compound (26.7 mg)

LCMS: $t_{RET}$=4.22 min; MH$^+$=534

This racemic material was resolved by chiral HPLC on a 25×2 cm Chiralcel OD column eluted with heptane:EtOH 85:15 with a flow rate of 15 mL/min to provide Example 26-A (enantiomer A, 6.3 mg) and Example 26-B (enantiomer B, 6.2 mg)

Example 26-A (Enantiomer A)

Analytical chiral HPLC (25×0.46 cm Chiralcel OD column, heptane:EtOH 85:15 eluting at 1 mL/min): $t_{RET}$=5.0 min
LCMS: $t_{RET}$=4.22 min; MH$^+$=534

Example 26-B (Enantiomer B)

Analytical chiral HPLC (25×0.46 cm Chiralcel OD column, heptane:EtOH 85:15 eluting at 1 mL/min): $t_{RET}$=6.8 min LCMS: $t_{RET}$=4.22 min; $MH^+$=534

Example 27

Ethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate

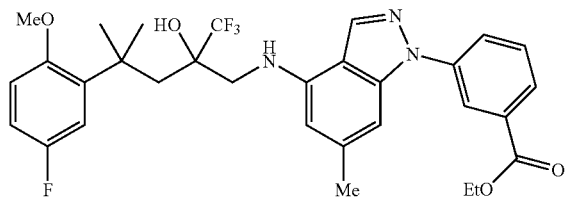

Sodium tert-butoxide (4 mg, 0.042 mmol) was added to a solution of phenylmethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate (Intermediate 30, 23 mg, 0.035 mmol) in ethanol (3 mL) and the mixture stirred at room temperature for 75 min. The mixture was then partitioned between dichloromethane (20 mL) and aqueous ammonium chloride (20 mL). The organic layer was separated, passed through a hydrophobic frit and evaporated and the residue purified by mass-directed autopreparation to give the title compound (12 mg).

LCMS: $t_{RET}$=4.35 min; $MH^+$=588

Example 28

4-(2,3-Dihydro-1-benzofuran-7-yl)-1,1,1-trifluoro-4-methyl-2-[({1-[4-(methyloxy)phenyl]-1H-indazol-4-yl}amino)methyl]-2-pentanol

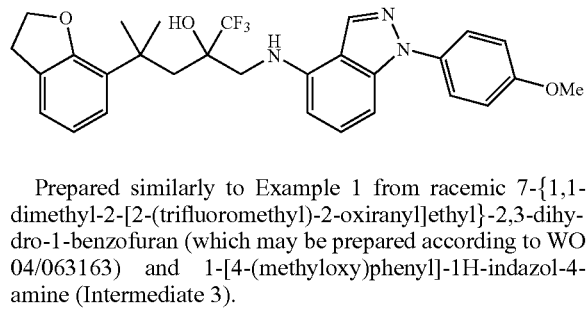

Prepared similarly to Example 1 from racemic 7-{1,1-dimethyl-2-[2-(trifluoromethyl)-2-oxiranyl]ethyl}-2,3-dihydro-1-benzofuran (which may be prepared according to WO 04/063163) and 1-[4-(methyloxy)phenyl]-1H-indazol-4-amine (Intermediate 3).

LCMS: $t_{RET}$=3.99 min; $MH^+$=526

BIOLOGICAL EXPERIMENTAL

Glucocorticoid Receptor Binding Assay

The ability of compounds to bind to the glucocorticoid receptor was determined by assessing their ability to compete with an Alexa 555 fluorescently-labelled dexamethasone derivative. Compounds were solvated and diluted in DMSO, and transferred directly into assay plates. Fluorescent dexamethasone and a partially purified full length glucocorticoid receptor were added to the plates, together with buffer components to stabilise the GR protein and incubated at room temperature for 2 hrs in the dark. Binding of each compound was assessed by analysing the displacement of fluorescent ligand by measuring the decrease in fluorescence polarisation signal from the mixture.

Examples 1, 1-A, 2, 2-B, 3, 4, 4-B, 5, 6, 6-A, 7 to 14, 14-B, 15, 15-B, 16, 16-A, 17, 17-A, 17-B, 18 to 24, 24-A, 24-B, 25, 25-A, 26-B, 27 and 28 have glucocorticoid binding with a $pIC_{50}$>7 in this assay.

Glucocorticoid Mediated Transrepression of NFkB Activity

Human A549 lung epithelial cells were engineered to contain a secreted placental alkaline phosphatase gene under the control of the distal region of the NFkB dependent ELAM promoter as previously described in Ray, K. P., Farrow, S., Daly, M., Talabot, F. and Searle, N. "Induction of the E-selectin promoter by interleukin 1 and tumour necrosis factor alpha, and inhibition by glucocorticoids" Biochemical Journal (1997) 328: 707-15.

Compounds were solvated and diluted in DMSO, and transferred directly into assay plates such that the final concentration of DMSO was 0.7%. Following the addition of cells (40K per well), plates were incubated for 1 hr prior to the addition of 3 ng/ml human recombinant TNFα. Following continued incubation for 16 hr, alkaline phosphatase activity was determined by measuring the change in optical density at 405 nM with time following the addition of 0.7 volumes of assay buffer (1 mg/ml p-nitrophenylphosphate dissolved in 1M diethanolamine, 0.28M NaCl, 0.5 mM $MgCl_2$). Dose response curves were constructed from which $EC_{50}$ values were estimated.

Examples 1, 1-A, 2, 2-B, 3, 4, 4-B, 5, 6, 6-B, 7 to 14, 14-B, 15, 15-B, 16, 16-A, 17, 17-B, 18 to 24, 24-B, 25, 25-A, 26-B, 27 and 28 show $pEC_{50}$>8.5 in this assay.

Examples 4-B, 15-B, 16-A, 17, 17-B, 20, 21, 24, 24-B, 25-A and 26B show $pEC_{50}$>9.5 in this assay Assay for Progesterone Receptor Activity A T225 flask of CV-1 cells at a density of 80% confluency was washed with PBS, detached from the flask using 0.25% trypsin and counted using a Sysmex KX-21N. Cells were diluted in DMEM containing 10% Hyclone, 2 mM L-Glutamate and 1% Pen/Strep at 140 cells/µl and transduced with 10% PRb-BacMam and 10% MMTV-BacMam. 70 ml of suspension cells were dispensed to each well of white Nunc 384-well plates, containing compounds at the required concentration. After 24 h 10 µl of Steady Glo were added to each well of the plates. Plates were incubated in the dark for 10 min before reading them on a Viewlux reader. Dose response curves were constructed from which $pEC_{50}$ values were estimated.

Examples 2A, 3, 4A, 5, 6A, 7, 15A, 16B, 24A, 25B and 26A show $pEC_{50}$<5 in this assay.

In describing those examples which are preferred or more preferred according to their activity in the assays above, it will be appreciated that at least one isomer, for example, an enantiomer in a mixture of isomers (such as a racemate) has the described activity. The other enantiomer may have similar activity, less activity, no activity or may have some antagonist activity in the case of a functional assay.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part, may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

The invention claimed is:

1. A compound of formula (I):

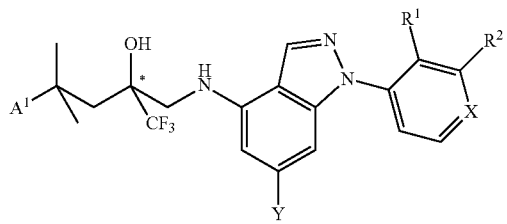

* = chiral centre wherein
A$^1$ represents 5-fluoro-2-methoxy-phenyl or 5-fluoro-2-hydroxy-phenyl;
X represents —C(R$^3$)—;
when X represents —C(R$^3$)—, R$^2$ represents hydrogen and R$^1$ represents fluorine, R$^3$ represents hydrogen or fluorine,
when X represents —C(R$^3$)— and R$^2$ and R$^1$ each represent hydrogen, R$^3$ represents hydrogen, hydroxy, methoxy or fluorine,
when X represents —C(R$^3$)— and R$^2$ represents hydroxy, methoxy, —CO$_2$CH$_3$ or —CO$_2$CH$_2$CH$_3$, R$^1$ and R$^3$ each represent hydrogen; and
Y represents H or methyl;
or salts thereof.

2. A compound according to claim 1 wherein A$^1$ represents 5-fluoro-2-hydroxy-phenyl.

3. A compound according to claim 1 wherein A$^1$ represents 5-fluoro-2-methoxy-phenyl.

4. A compound according to claim 1 wherein X represents —C(R$^3$)—, R$^2$ represents hydrogen, R$^1$ represents fluorine and R$^3$ represents hydrogen or fluorine.

5. A compound according to claim 4 wherein R$^3$ represents fluorine.

6. A compound according to claim 1 wherein X represents —C(R$^3$)—, R$^2$ and R$^1$ each represent hydrogen and R$^3$ represents hydrogen, hydroxy, methoxy or fluorine.

7. A compound according to claim 1 wherein X represents —C(R$^3$)—, R$^2$ represents hydroxy, methoxy, —CO$_2$CH$_3$ or —CO$_2$CH$_2$CH$_3$, and R$^1$ and R$^3$ each represent hydrogen.

8. A compound according to claim 1 wherein Y represents methyl.

9. A compound which is selected from the group consisting of:
2-({[1-(2,4-difluorophenyl)-1H-indazol-4-yl]amino}methyl)-1,1,1-trifluoro-4-[5-fluoro-2-(methyloxy)phenyl]-4-methyl-2-pentanol which showed a retention time of 5.19 min on analytical chiral HPLC (25×0.46 cm Chiralcel OD column, heptane:EtOH 7:3, eluting at 1 ml/min);
1,1,1-trifluoro-4-[5-fluoro-2-(methyloxy)phenyl]-4-methyl-2-{[(6-methyl-1-phenyl-1H-indazol-4-yl)amino]methyl}-2-pentanol which showed a retention time of 6.64 min on analytical chiral HPLC (25×0.46 cm Chiralcel OD-H column, heptane:EtOH 4:1 eluting at 1 mL/min);
(2R) 2-({[1-(2,4-difluorophenyl)-6-methyl-1H-indazol-4-yl]amino}methyl)-1,1,1-trifluoro-4-[5-fluoro-2-(methyloxy)phenyl]-4-methyl-2-pentanol;
4-(2,3-dihydro-1-benzofuran-7-yl)-1,1,1-trifluoro-4-methyl-2-{[(6-methyl-1-phenyl-1H-indazol-4-yl)amino]methyl}-2-pentanol;
(2R) 4-(2,3-dihydro-1-benzofuran-7-yl)-1,1,1-trifluoro-4-methyl-2-{[(6-methyl-1-phenyl-1H-indazol-4-yl)amino]methyl}-2-pentanol;
4-(4-{[4-[5-fluoro-2-(methyloxy)phenyl]-2-hydroxy-4-methyl-2-(trifluoromethyl)pentyl]amino}-6-methyl-1H-indazol-1-yl)phenol;
4-fluoro-2-[4,4,4-trifluoro-3-hydroxy-3-({[1-(4-hydroxyphenyl)-6-methyl-1H-indazol-4-yl]amino}methyl)-1,1-dimethylbutyl]phenol;
4-fluoro-2-[4,4,4-trifluoro-3-hydroxy-3-({[1-(3-hydroxyphenyl)-6-methyl-1H-indazol-4-yl]amino}methyl)-1,1-dimethylbutyl]phenol;
4-fluoro-2-[4,4,4-trifluoro-3-hydroxy-3-({[1-(3-hydroxyphenyl)-6-methyl-1H-indazol-4-yl]amino}methyl)-1,1-dimethylbutyl]phenol which showed a retention time of 13.77 min on analytical chiral HPLC (25×0.46 cm Chiralpak AD column, heptane:EtOH 3:1 eluting at 1 mL/min);
1,1,1-trifluoro-4-[5-fluoro-2-(methyloxy)phenyl]-2-({[1-(2-fluorophenyl)-6-methyl-1H-indazol-4-yl]amino}methyl)-4-methyl-2-pentanol, which showed a retention time of 7.4 min on analytical chiral HPLC (25×0.46 cm Chiralcel OJ column, heptane:EtOH 7:3 eluting at 1 mL/min);
1,1,1-trifluoro-4-[5-fluoro-2-(methyloxy)phenyl]-2-({[1-(4-fluorophenyl)-6-methyl-1H-indazol-4-yl]amino}methyl)-4-methyl-2-pentanol, which showed a retention time of 6.8 min on analytical chiral HPLC (25×0.46 cm Chiralcel OD column, heptane:EtOH 85:15 eluting at 1 mL/min);
and salts thereof.

10. A pharmaceutical composition comprising a compound as claimed in claim 1, in admixture with one or more physiologically acceptable diluents or carriers.

11. A pharmaceutical aerosol formulation comprising a compound as claimed in claim 1 and a fluorocarbon or hydrogen-containing chlorofluorocarbon or mixtures thereof as propellant, optionally in combination with a surfactant and/or a cosolvent.

12. A pharmaceutical aerosol formulation as claimed in claim 11 wherein the propellant is selected from the group consisting of 1,1,1,2-tetrafluoroethane, 1,1,1,2,3,3,3-heptafluoro-n-propane and mixtures thereof.

* * * * *